United States Patent
Reicher et al.

(10) Patent No.: US 9,754,074 B1
(45) Date of Patent: *Sep. 5, 2017

(54) SMART PLACEMENT RULES

(71) Applicant: DR Systems, Inc., San Diego, CA (US)

(72) Inventors: Murray A. Reicher, Rancho Santa Fe, CA (US); Cole A. Genovese, Encinitas, CA (US); Carol G. Sloyer, La Jolla, CA (US); Thomas J. Edwards, San Diego, CA (US)

(73) Assignee: D.R. Systems, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/298,806

(22) Filed: Jun. 6, 2014

Related U.S. Application Data

(63) Continuation of application No. 13/907,128, filed on May 31, 2013, now Pat. No. 8,751,268, which is a continuation of application No. 13/118,085, filed on May 27, 2011, now Pat. No. 8,457,990, which is a continuation of application No. 11/942,674, filed on Nov. 19, 2007, now Pat. No. 7,953,614.

(60) Provisional application No. 60/867,071, filed on Nov. 22, 2006.

(51) Int. Cl.
G06Q 10/00 (2012.01)
G06F 19/00 (2011.01)

(52) U.S. Cl.
CPC .......... *G06F 19/321* (2013.01); *G06F 19/322* (2013.01)

(58) Field of Classification Search
CPC ......... G06Q 50/22; G06Q 50/24; G06Q 10/10

USPC ............................................................ 705/3
See application file for complete search history.

(56) References Cited

U.S. PATENT DOCUMENTS

| | | | |
|---|---|---|---|
| 4,672,683 | A | 6/1987 | Matsueda |
| 5,123,056 | A | 6/1992 | Wilson |
| 5,172,419 | A | 12/1992 | Manian |
| 5,179,651 | A | 1/1993 | Taaffe et al. |

(Continued)

FOREIGN PATENT DOCUMENTS

WO  WO 2007/131157  11/2007

OTHER PUBLICATIONS

US 7,801,341, 09/2010, Fram et al. (withdrawn)

(Continued)

*Primary Examiner* — Hiep V Nguyen
(74) *Attorney, Agent, or Firm* — Knobbe, Martens, Olson & Bear, LLP

(57) ABSTRACT

A smart placement module determines components of received medical data, such as medical reports and image montages, to forward to one or more secondary location, such as an EMR system, based on smart placement rules that are established by a user that receives the medical data, such as a referring doctor. Thus, the smart placement module decreases or removes the need for the receiving user to manually select and transfer certain medical data for storage at the EMR system. Accordingly, the receiving user, and other authorized EMR system users, may have prompt access to the medical data via their respective connections to the EMR system. In one embodiment, the smart placement module transmits a patient identification file that is usable by the receiving EMR system to allow the EMR system to associate received medical data with other data regarding a respective patient.

22 Claims, 4 Drawing Sheets

(56) References Cited

U.S. PATENT DOCUMENTS

| | | |
|---|---|---|
| 5,431,161 A | 7/1995 | Ryals et al. |
| 5,452,416 A | 9/1995 | Hilton et al. |
| 5,515,375 A | 5/1996 | DeClerck |
| 5,542,003 A | 7/1996 | Wofford |
| 5,734,915 A | 3/1998 | Roewer |
| 5,740,267 A | 4/1998 | Echerer et al. |
| 5,779,634 A | 7/1998 | Ema et al. |
| 5,807,256 A | 9/1998 | Taguchi |
| 5,835,030 A | 11/1998 | Tsutsui et al. |
| 5,852,646 A | 12/1998 | Klotz et al. |
| 5,857,030 A | 1/1999 | Gaborski |
| 5,926,568 A | 7/1999 | Chaney et al. |
| 5,954,650 A | 9/1999 | Saito et al. |
| 5,976,088 A | 11/1999 | Urbano et al. |
| 5,986,662 A | 11/1999 | Argiro et al. |
| 5,987,345 A | 11/1999 | Engelmann et al. |
| 5,995,644 A | 11/1999 | Lai et al. |
| 6,008,813 A | 12/1999 | Lauer et al. |
| 6,115,486 A | 9/2000 | Cantoni |
| 6,128,002 A | 10/2000 | Leiper |
| 6,130,671 A | 10/2000 | Argiro |
| 6,151,581 A | 11/2000 | Kraftson et al. |
| 6,175,643 B1 | 1/2001 | Lai et al. |
| 6,177,937 B1 | 1/2001 | Stockham et al. |
| 6,185,320 B1 | 2/2001 | Bick et al. |
| 6,211,884 B1 | 4/2001 | Knittel et al. |
| 6,219,059 B1 | 4/2001 | Argiro |
| 6,219,061 B1 | 4/2001 | Lauer et al. |
| 6,243,095 B1 | 6/2001 | Shile et al. |
| 6,243,098 B1 | 6/2001 | Lauer et al. |
| 6,262,740 B1 | 7/2001 | Lauer et al. |
| 6,266,733 B1 | 7/2001 | Knittel et al. |
| 6,269,379 B1 | 7/2001 | Hiyama et al. |
| 6,297,799 B1 | 10/2001 | Knittel et al. |
| 6,304,667 B1 | 10/2001 | Reitano |
| 6,310,620 B1 | 10/2001 | Lauer et al. |
| 6,313,841 B1 | 11/2001 | Ogata et al. |
| 6,342,885 B1 | 1/2002 | Knittel et al. |
| 6,347,329 B1 | 2/2002 | Evans |
| 6,351,547 B1 | 2/2002 | Johnson et al. |
| 6,356,265 B1 | 3/2002 | Knittel et al. |
| 6,369,816 B1 | 4/2002 | Knittel et al. |
| 6,383,135 B1 | 5/2002 | Chikovani et al. |
| 6,388,687 B1 | 5/2002 | Brackett et al. |
| 6,404,429 B1 | 6/2002 | Knittel |
| 6,407,737 B1 | 6/2002 | Zhao et al. |
| 6,411,296 B1 | 6/2002 | Knittel et al. |
| 6,421,057 B1 | 7/2002 | Lauer et al. |
| 6,424,346 B1 | 7/2002 | Correll et al. |
| 6,424,996 B1 | 7/2002 | Killcommons et al. |
| 6,426,749 B1 | 7/2002 | Knittel et al. |
| 6,427,022 B1 | 7/2002 | Craine et al. |
| 6,438,533 B1 | 8/2002 | Spackman et al. |
| 6,463,169 B1 | 10/2002 | Ino et al. |
| 6,476,810 B1 | 11/2002 | Simha et al. |
| 6,512,517 B1 | 1/2003 | Knittel et al. |
| 6,532,299 B1 | 3/2003 | Sachdeva et al. |
| 6,532,311 B1 | 3/2003 | Pritt |
| 6,556,695 B1 | 4/2003 | Packer et al. |
| 6,556,724 B1 | 4/2003 | Chang et al. |
| 6,563,950 B1 | 5/2003 | Wiskott et al. |
| 6,574,629 B1 | 6/2003 | Cooke et al. |
| 6,577,753 B2 | 6/2003 | Ogawa |
| 6,603,494 B1 | 8/2003 | Banks et al. |
| 6,606,171 B1 | 8/2003 | Renk et al. |
| 6,614,447 B1 | 9/2003 | Bhatia et al. |
| 6,618,060 B1 | 9/2003 | Brackett |
| 6,621,918 B1 | 9/2003 | Hu et al. |
| 6,630,937 B2 | 10/2003 | Kallergi et al. |
| 6,650,766 B1 | 11/2003 | Rogers |
| 6,654,012 B1 | 11/2003 | Lauer et al. |
| 6,678,764 B2 | 1/2004 | Parvelescu et al. |
| 6,680,735 B1 | 1/2004 | Seiler et al. |
| 6,683,933 B2 | 1/2004 | Saito et al. |
| 6,697,067 B1 | 2/2004 | Callahan et al. |
| 6,697,506 B1 | 2/2004 | Qian et al. |
| 6,734,880 B2 | 5/2004 | Chang et al. |
| 6,760,755 B1 | 7/2004 | Brackett |
| 6,775,402 B2 | 8/2004 | Bacus et al. |
| 6,778,689 B1 | 8/2004 | Aksit et al. |
| 6,820,093 B2 | 11/2004 | de la Huerga |
| 6,820,100 B2 | 11/2004 | Funahashi |
| 6,826,297 B2 | 11/2004 | Saito et al. |
| 6,829,377 B2 | 12/2004 | Milioto |
| 6,864,794 B2 | 3/2005 | Betz |
| 6,886,133 B2 | 4/2005 | Bailey et al. |
| 6,891,920 B1 | 5/2005 | Minyard et al. |
| 6,894,707 B2 | 5/2005 | Nemoto |
| 6,909,436 B1 | 6/2005 | Pianykh et al. |
| 6,909,795 B2 | 6/2005 | Tecotzky et al. |
| 6,917,696 B2 | 7/2005 | Soenksen |
| 6,988,075 B1 | 1/2006 | Hacker |
| 6,996,205 B2 | 2/2006 | Capolunghi et al. |
| 7,016,952 B2 | 3/2006 | Mullen et al. |
| 7,022,073 B2 | 4/2006 | Fan et al. |
| 7,027,633 B2 | 4/2006 | Foran et al. |
| 7,031,504 B1 | 4/2006 | Argiro et al. |
| 7,031,846 B2 | 4/2006 | Kaushikkar et al. |
| 7,039,723 B2 | 5/2006 | Hu et al. |
| 7,043,474 B2 | 5/2006 | Mojsilovic |
| 7,050,620 B2 | 5/2006 | Heckman |
| 7,054,473 B1 | 5/2006 | Roehrig et al. |
| 7,058,901 B1 | 6/2006 | Hafey et al. |
| 7,092,572 B2 | 8/2006 | Huang et al. |
| 7,103,205 B2 | 9/2006 | Wang et al. |
| 7,106,479 B2 | 9/2006 | Roy et al. |
| 7,110,616 B2 | 9/2006 | Ditt et al. |
| 7,113,186 B2 | 9/2006 | Kim et al. |
| 7,136,064 B2 | 11/2006 | Zuiderveld |
| 7,139,416 B2 | 11/2006 | Vuylsteke |
| 7,149,334 B2 | 12/2006 | Dehmeshki |
| 7,155,043 B2 | 12/2006 | Daw |
| 7,162,623 B2 | 1/2007 | Yngvesson |
| 7,170,532 B2 | 1/2007 | Sako |
| 7,174,054 B2 | 2/2007 | Manber et al. |
| 7,209,149 B2 | 4/2007 | Jogo |
| 7,209,578 B2 | 4/2007 | Saito et al. |
| 7,212,661 B2 | 5/2007 | Samara et |
| 7,218,763 B2 | 5/2007 | Belykh et al. |
| 7,224,852 B2 | 5/2007 | Lipton et al. |
| 7,236,558 B2 | 6/2007 | Saito et al. |
| 7,260,249 B2 | 8/2007 | Smith |
| 7,263,710 B1 | 8/2007 | Hummel et al. |
| 7,272,610 B2 | 9/2007 | Torres |
| 7,346,199 B2 | 3/2008 | Pfaff |
| 7,366,992 B2 | 4/2008 | Thomas, III |
| 7,379,578 B2 | 5/2008 | Soussaline et al. |
| 7,412,111 B2 | 8/2008 | Battle et al. |
| 7,450,747 B2 | 11/2008 | Jabri et al. |
| 7,492,970 B2 | 2/2009 | Saito et al. |
| 7,505,782 B2 | 3/2009 | Chu |
| 7,516,417 B2 | 4/2009 | Amador et al. |
| 7,525,554 B2 | 4/2009 | Morita et al. |
| 7,526,114 B2 | 4/2009 | Seul et al. |
| 7,526,132 B2 | 4/2009 | Koenig |
| 7,545,965 B2 | 6/2009 | Suzuki et al. |
| 7,574,029 B2 | 8/2009 | Peterson et al. |
| 7,583,861 B2 | 9/2009 | Hanna et al. |
| 7,590,272 B2 | 9/2009 | Brejl et al. |
| 7,613,335 B2 | 11/2009 | McLennan et al. |
| 7,634,121 B2 | 12/2009 | Novatzky et al. |
| 7,636,413 B2 | 12/2009 | Toth |
| 7,639,879 B2 | 12/2009 | Goto et al. |
| 7,656,543 B2 | 2/2010 | Atkins |
| 7,660,481 B2 | 2/2010 | Schaap et al. |
| 7,660,488 B2 | 2/2010 | Reicher et al. |
| 7,668,352 B2 | 2/2010 | Tecotzky et al. |
| 7,683,909 B2 | 3/2010 | Takekoshi |
| 7,698,152 B2 | 4/2010 | Reid |
| 7,716,277 B2 | 5/2010 | Yamatake |
| 7,787,672 B2 | 8/2010 | Reicher et al. |
| 7,834,891 B2 | 11/2010 | Yarger et al. |
| 7,835,560 B2 | 11/2010 | Vining et al. |
| 7,885,440 B2 | 2/2011 | Fram et al. |

(56) References Cited

U.S. PATENT DOCUMENTS

| | | |
|---|---|---|
| 7,885,828 B2 | 2/2011 | Glaser-Seidnitzer et al. |
| 7,899,514 B1 | 3/2011 | Kirkland |
| 7,920,152 B2 | 4/2011 | Fram et al. |
| 7,953,614 B1 | 5/2011 | Reicher |
| 7,970,188 B2 | 6/2011 | Mahesh et al. |
| 7,970,625 B2 | 6/2011 | Reicher et al. |
| 7,991,210 B2 | 8/2011 | Peterson et al. |
| 7,992,100 B2 | 8/2011 | Lundstrom et al. |
| 8,019,138 B2 | 9/2011 | Reicher et al. |
| 8,046,044 B2 | 10/2011 | Stazzone et al. |
| 8,050,938 B1 | 11/2011 | Green, Jr. et al. |
| 8,065,166 B2 | 11/2011 | Maresh et al. |
| 8,073,225 B2 | 12/2011 | Hagen et al. |
| 8,094,901 B1 | 1/2012 | Reicher et al. |
| 8,150,708 B2 | 4/2012 | Kotula et al. |
| 8,214,756 B2 | 7/2012 | Salazar-Ferrer et al. |
| 8,217,966 B2 | 7/2012 | Fram et al. |
| 8,244,014 B2 | 8/2012 | Reicher et al. |
| 8,249,687 B2 | 8/2012 | Peterson et al. |
| 8,262,572 B2 | 9/2012 | Chono |
| 8,292,811 B2 | 10/2012 | Relkuntwar et al. |
| 8,370,293 B2 | 2/2013 | Iwase et al. |
| 8,379,051 B2 | 2/2013 | Brown |
| 8,380,533 B2 | 2/2013 | Reicher et al. |
| 8,391,643 B2 | 3/2013 | Melbourne et al. |
| 8,406,491 B2 | 3/2013 | Gee et al. |
| 8,457,990 B1 | 6/2013 | Reicher et al. |
| 8,554,576 B1 | 10/2013 | Reicher et al. |
| 8,560,050 B2 | 10/2013 | Martin et al. |
| 8,610,746 B2 | 12/2013 | Fram et al. |
| 8,626,527 B1 | 1/2014 | Reicher |
| 8,693,757 B2 | 4/2014 | Gundel |
| 8,712,120 B1 | 4/2014 | Reicher |
| 8,731,259 B2 | 5/2014 | Reicher et al. |
| 8,751,268 B1 | 6/2014 | Reicher |
| 8,797,350 B2 | 8/2014 | Fram |
| 8,879,807 B2 | 11/2014 | Fram et al. |
| 8,913,808 B2 | 12/2014 | Reicher et al. |
| 9,042,617 B1 | 5/2015 | Reicher et al. |
| 9,324,188 B1 | 4/2016 | Fram et al. |
| 9,386,084 B1 | 7/2016 | Reicher et al. |
| 9,471,210 B1 | 10/2016 | Fram et al. |
| 9,495,604 B1 | 11/2016 | Fram |
| 9,501,617 B1 | 11/2016 | Reicher et al. |
| 9,501,627 B2 | 11/2016 | Reicher et al. |
| 9,501,863 B1 | 11/2016 | Fram et al. |
| 9,536,324 B1 | 1/2017 | Fram |
| 9,542,082 B1 | 1/2017 | Reicher et al. |
| 9,672,477 B1 | 6/2017 | Reicher et al. |
| 9,684,762 B2 | 6/2017 | Reicher et al. |
| 2001/0016822 A1 | 8/2001 | Bessette |
| 2001/0042124 A1 | 11/2001 | Barron |
| 2002/0016718 A1 | 2/2002 | Rothschild et al. |
| 2002/0021828 A1 | 2/2002 | Papier et al. |
| 2002/0039084 A1 | 4/2002 | Yamaguchi |
| 2002/0044696 A1 | 4/2002 | Sirohey et al. |
| 2002/0070970 A1 | 6/2002 | Wood et al. |
| 2002/0073429 A1 | 6/2002 | Beane et al. |
| 2002/0090118 A1 | 7/2002 | Olschewski |
| 2002/0090119 A1 | 7/2002 | Saito et al. |
| 2002/0090124 A1 | 7/2002 | Soubelet et al. |
| 2002/0091659 A1 | 7/2002 | Beaulieu et al. |
| 2002/0103673 A1 | 8/2002 | Atwood |
| 2002/0103827 A1 | 8/2002 | Sesek |
| 2002/0110285 A1 | 8/2002 | Wang et al. |
| 2002/0144697 A1 | 10/2002 | Betz |
| 2002/0172408 A1 | 11/2002 | Saito et al. |
| 2002/0172409 A1 | 11/2002 | Saito et al. |
| 2002/0180883 A1 | 12/2002 | Tomizawa et al. |
| 2002/0186820 A1 | 12/2002 | Saito et al. |
| 2002/0190984 A1 | 12/2002 | Seiler et al. |
| 2003/0005464 A1* | 1/2003 | Gropper et al. ............ 725/115 |
| 2003/0013951 A1 | 1/2003 | Stefanescu |
| 2003/0016850 A1 | 1/2003 | Kaufman et al. |
| 2003/0028402 A1 | 2/2003 | Ulrich et al. |
| 2003/0034973 A1 | 2/2003 | Zuiderveld |
| 2003/0037054 A1 | 2/2003 | Dutta et al. |
| 2003/0055896 A1 | 3/2003 | Hu et al. |
| 2003/0065613 A1 | 4/2003 | Smith |
| 2003/0071829 A1 | 4/2003 | Bodicker et al. |
| 2003/0101291 A1 | 5/2003 | Mussack et al. |
| 2003/0115083 A1 | 6/2003 | Masarie et al. |
| 2003/0120516 A1 | 6/2003 | Perednia |
| 2003/0130973 A1 | 7/2003 | Sumner, II et al. |
| 2003/0140141 A1 | 7/2003 | Mullen et al. |
| 2003/0156745 A1 | 8/2003 | Saito et al. |
| 2003/0160095 A1 | 8/2003 | Segal |
| 2003/0164860 A1 | 9/2003 | Shen et al. |
| 2003/0184778 A1 | 10/2003 | Chiba |
| 2003/0187689 A1 | 10/2003 | Barnes et al. |
| 2003/0190062 A1 | 10/2003 | Noro et al. |
| 2003/0204420 A1 | 10/2003 | Wilkes et al. |
| 2003/0215122 A1 | 11/2003 | Tanaka |
| 2004/0015703 A1 | 1/2004 | Madison et al. |
| 2004/0024303 A1 | 2/2004 | Banks et al. |
| 2004/0086163 A1 | 5/2004 | Moriyama et al. |
| 2004/0088192 A1 | 5/2004 | Schmidt et al. |
| 2004/0105030 A1 | 6/2004 | Yamane |
| 2004/0105574 A1 | 6/2004 | Pfaff |
| 2004/0114714 A1 | 6/2004 | Minyard et al. |
| 2004/0122705 A1 | 6/2004 | Sabol et al. |
| 2004/0143582 A1 | 7/2004 | Vu |
| 2004/0161164 A1 | 8/2004 | Dewaele |
| 2004/0165791 A1 | 8/2004 | Kaltanji |
| 2004/0172306 A1 | 9/2004 | Wohl |
| 2004/0174429 A1 | 9/2004 | Chu |
| 2004/0190780 A1 | 9/2004 | Shiibashi et al. |
| 2004/0202387 A1 | 10/2004 | Yngvesson |
| 2004/0243435 A1 | 12/2004 | Williams |
| 2004/0252871 A1 | 12/2004 | Tecotzky et al. |
| 2004/0254816 A1 | 12/2004 | Myers |
| 2004/0255252 A1 | 12/2004 | Rodriguez |
| 2005/0010531 A1 | 1/2005 | Kushalnagar et al. |
| 2005/0027569 A1 | 2/2005 | Gollogly |
| 2005/0027570 A1 | 2/2005 | Maier et al. |
| 2005/0043970 A1 | 2/2005 | Hsieh |
| 2005/0063575 A1 | 3/2005 | Ma et al. |
| 2005/0065424 A1 | 3/2005 | Shah et al. |
| 2005/0074150 A1 | 4/2005 | Bruss |
| 2005/0074157 A1 | 4/2005 | Thomas, III |
| 2005/0075544 A1 | 4/2005 | Shapiro et al. |
| 2005/0088534 A1 | 4/2005 | Shen et al. |
| 2005/0107689 A1 | 5/2005 | Sasano |
| 2005/0108058 A1 | 5/2005 | Weidner et al. |
| 2005/0110791 A1 | 5/2005 | Krishnamoorthy et al. |
| 2005/0111733 A1 | 5/2005 | Fors et al. |
| 2005/0113681 A1 | 5/2005 | DeFreitas et al. |
| 2005/0114178 A1 | 5/2005 | Krishnamurthy et al. |
| 2005/0114179 A1 | 5/2005 | Brackett et al. |
| 2005/0114283 A1 | 5/2005 | Pearson et al. |
| 2005/0143654 A1 | 6/2005 | Zuiderveld et al. |
| 2005/0171818 A1 | 8/2005 | McLaughlin |
| 2005/0184988 A1 | 8/2005 | Yanof et al. |
| 2005/0197860 A1* | 9/2005 | Joffe et al. ............ 705/2 |
| 2005/0238218 A1 | 10/2005 | Nakamura |
| 2005/0244041 A1 | 11/2005 | Tecotzky et al. |
| 2005/0251013 A1 | 11/2005 | Krishnan |
| 2005/0254729 A1 | 11/2005 | Saito et al. |
| 2005/0273009 A1 | 12/2005 | Deischinger et al. |
| 2006/0008181 A1 | 1/2006 | Takekoshi |
| 2006/0031097 A1 | 2/2006 | Lipscher et al. |
| 2006/0050152 A1 | 3/2006 | Rai et al. |
| 2006/0058603 A1 | 3/2006 | Dave et al. |
| 2006/0061570 A1 | 3/2006 | Cheryauka et al. |
| 2006/0095426 A1 | 5/2006 | Takachio et al. |
| 2006/0111941 A1 | 5/2006 | Blom |
| 2006/0122482 A1 | 6/2006 | Mariotti et al. |
| 2006/0171574 A1 | 8/2006 | DelMonego et al. |
| 2006/0181548 A1 | 8/2006 | Hafey |
| 2006/0188134 A1 | 8/2006 | Quist |
| 2006/0230072 A1 | 10/2006 | Partovi et al. |
| 2006/0241979 A1 | 10/2006 | Sato et al. |
| 2006/0267976 A1 | 11/2006 | Saito et al. |
| 2006/0276708 A1 | 12/2006 | Peterson et al. |

(56) References Cited

U.S. PATENT DOCUMENTS

| | | |
|---|---|---|
| 2006/0277075 A1 | 12/2006 | Salwan |
| 2006/0282408 A1 | 12/2006 | Wisely et al. |
| 2007/0009078 A1 | 1/2007 | Saito et al. |
| 2007/0021977 A1 | 1/2007 | Elsholz |
| 2007/0050701 A1 | 3/2007 | El Emam et al. |
| 2007/0055550 A1 | 3/2007 | Courtney et al. |
| 2007/0064984 A1 | 3/2007 | Vassa et al. |
| 2007/0067124 A1 | 3/2007 | Kimpe et al. |
| 2007/0073556 A1 | 3/2007 | Lau et al. |
| 2007/0106535 A1 | 5/2007 | Matsunaga |
| 2007/0106633 A1 | 5/2007 | Reiner |
| 2007/0109299 A1 | 5/2007 | Peterson |
| 2007/0109402 A1 | 5/2007 | Niwa |
| 2007/0110294 A1 | 5/2007 | Schaap et al. |
| 2007/0116345 A1 | 5/2007 | Peterson et al. |
| 2007/0116346 A1 | 5/2007 | Peterson et al. |
| 2007/0122016 A1 | 5/2007 | Brejl et al. |
| 2007/0124541 A1 | 5/2007 | Lang et al. |
| 2007/0140536 A1 | 6/2007 | Sehnert |
| 2007/0159962 A1 | 7/2007 | Mathavu et al. |
| 2007/0162308 A1 | 7/2007 | Peters |
| 2007/0165917 A1 | 7/2007 | Cao et al. |
| 2007/0174079 A1 | 7/2007 | Kraus |
| 2007/0192138 A1 | 8/2007 | Saito et al. |
| 2007/0192140 A1 | 8/2007 | Gropper |
| 2007/0237380 A1 | 10/2007 | Iwase et al. |
| 2007/0239481 A1 | 10/2007 | DiSilvestro et al. |
| 2008/0016111 A1 | 1/2008 | Keen |
| 2008/0021877 A1 | 1/2008 | Saito et al. |
| 2008/0059245 A1 | 3/2008 | Sakaida et al. |
| 2008/0100612 A1 | 5/2008 | Dastmalchi et al. |
| 2008/0103828 A1 | 5/2008 | Squilla et al. |
| 2008/0125846 A1 | 5/2008 | Battle et al. |
| 2008/0126982 A1 | 5/2008 | Sadikali et al. |
| 2008/0136838 A1 | 6/2008 | Goede et al. |
| 2008/0275913 A1 | 11/2008 | van Arragon et al. |
| 2008/0279439 A1 | 11/2008 | Minyard et al. |
| 2008/0300484 A1 | 12/2008 | Wang et al. |
| 2009/0005668 A1 | 1/2009 | West et al. |
| 2009/0022375 A1 | 1/2009 | Fidrich |
| 2009/0028410 A1 | 1/2009 | Shimazaki |
| 2009/0080719 A1 | 3/2009 | Watt |
| 2009/0091566 A1 | 4/2009 | Turney et al. |
| 2009/0123052 A1 | 5/2009 | Ruth et al. |
| 2009/0129643 A1 | 5/2009 | Natanzon et al. |
| 2009/0132586 A1 | 5/2009 | Napora et al. |
| 2009/0150481 A1 | 6/2009 | Garcia et al. |
| 2009/0182577 A1 | 7/2009 | Squilla et al. |
| 2009/0198514 A1 | 8/2009 | Rhodes |
| 2009/0213034 A1 | 8/2009 | Wu et al. |
| 2009/0248442 A1 | 10/2009 | Pacheco et al. |
| 2009/0268986 A1 | 10/2009 | Holstein et al. |
| 2009/0326373 A1 | 12/2009 | Boese et al. |
| 2010/0053353 A1 | 3/2010 | Hunter et al. |
| 2010/0086182 A1 | 4/2010 | Luo et al. |
| 2010/0131887 A1 | 5/2010 | Salazar-Ferrer et al. |
| 2010/0198608 A1 | 8/2010 | Kaboff et al. |
| 2010/0211409 A1 | 8/2010 | Kotula et al. |
| 2010/0246981 A1 | 9/2010 | Hu et al. |
| 2010/0299157 A1 | 11/2010 | Fram et al. |
| 2011/0016430 A1 | 1/2011 | Fram |
| 2011/0110572 A1 | 5/2011 | Guehring et al. |
| 2011/0293162 A1 | 12/2011 | Pajeau |
| 2011/0316873 A1 | 12/2011 | Reicher |
| 2012/0070048 A1 | 3/2012 | Van Den Brink |
| 2012/0130729 A1 | 5/2012 | Raizada et al. |
| 2012/0136794 A1 | 5/2012 | Kushalnagar et al. |
| 2012/0163684 A1 | 6/2012 | Natanzon et al. |
| 2012/0284657 A1 | 11/2012 | Hafey et al. |
| 2013/0070998 A1 | 3/2013 | Shibata |
| 2013/0076681 A1 | 3/2013 | Sirpal et al. |
| 2013/0083023 A1 | 4/2013 | Fram |
| 2013/0159019 A1 | 6/2013 | Reicher et al. |
| 2013/0169661 A1 | 7/2013 | Reicher |
| 2013/0297331 A1 | 11/2013 | Zuehlsdorff et al. |
| 2014/0022194 A1 | 1/2014 | Ito |
| 2014/0142983 A1 | 5/2014 | Backhaus et al. |
| 2015/0101066 A1 | 4/2015 | Fram |
| 2015/0160848 A1 | 6/2015 | Gkanatsios et al. |
| 2016/0034110 A1 | 2/2016 | Edwards |
| 2016/0335395 A1 | 11/2016 | Wu et al. |
| 2017/0038951 A1 | 2/2017 | Reicher |
| 2017/0039321 A1 | 2/2017 | Reicher |
| 2017/0039322 A1 | 2/2017 | Reicher |
| 2017/0039350 A1 | 2/2017 | Reicher |
| 2017/0039705 A1 | 2/2017 | Fram |
| 2017/0046014 A1 | 2/2017 | Fram |
| 2017/0046483 A1 | 2/2017 | Reicher |
| 2017/0046495 A1 | 2/2017 | Fram |
| 2017/0046870 A1 | 2/2017 | Fram |
| 2017/0053404 A1 | 2/2017 | Reicher |

OTHER PUBLICATIONS

US 8,208,705, 06/2012, Reicher et al. (withdrawn)
Interview Summary dated May 31, 2011 in U.S. Appl. No. 12/702,976.
Notice of Allowance dated Jul. 20, 2011, in U.S. Appl. No. 12/702,976.
Office Action dated Dec. 1, 2011, in U.S. Appl. No. 13/228,349.
Notice of Allowance dated Feb. 6, 2012, in U.S. Appl. No. 13/228,349.
Notice of Allowance dated Jul. 20, 2012, in U.S. Appl. No. 13/228,349.
Notice of Allowance dated May 17, 2010, in U.S. Appl. No. 11/268,261.
Supplemental Notice of Allowance dated Aug. 6, 2010, in U.S. Appl. No. 11/268,261.
Office Action dated May 16, 2011, in U.S. Appl. No. 12/857,915.
Interview Summary dated Sep. 6, 2011, in U.S. Appl. No. 12/857,915.
Final Office Action dated Dec. 15, 2011, in U.S. Appl. No. 12/857,915.
Office Action dated Jun. 12, 2012, in U.S. Appl. No. 12/857,915.
Office Action dated Aug. 23, 2013, in U.S. Appl. No. 12/857,915.
Notice of Allowance dated May 26, 2011 in U.S. Appl. No. 11/265,979.
Office Action dated Jun. 8, 2012 in U.S. Appl. No. 13/171,081.
Interview Summary dated Jul. 31, 2012 in U.S. Appl. No. 13/171,081.
Final Office Action dated Oct. 12, 2012 in U.S. Appl. No. 13/171,081.
Interview Summary dated Nov. 6, 2012 in U.S. Appl. No. 13/171,081.
Notice of Allowance, dated Sep. 4, 2013, in U.S. Appl. No. 13/171,081.
Non-Final Office Action dated Jan. 11, 2012 in U.S. Appl. No. 13/079,597.
Notice of Allowance dated Apr. 25, 2012, in U.S. Appl. No. 13/079,597.
Non-Final Office Action dated Apr. 4, 2013 in U.S. Appl. No. 13/535,758.
Notice of Allowance, dated Aug. 23, 2013 in U.S. Appl. No. 13/535,758.
Non-Final Office Action dated May 5, 2011 in U.S. Appl. No. 12/870,645.
Non-Final Office Action dated May 31, 2013, in U.S. Appl. No. 13/345,606.
Interview Summary dated Aug. 15, 2013, in U.S. Appl. No. 13/345,606.
Non Final Office Action Dated Nov. 10, 2011 in U.S. Appl. No. 13/118,085.
Interview Summary, dated Feb. 17, 2012, in U.S. Appl. No. 13/118,085.
Final Office Action, dated Apr. 13, 2012, in U.S. Appl. No. 13/118,085.
Notice of Allowance, dated Feb. 6, 2013, in U.S. Appl. No. 13/118,085.

(56) References Cited

OTHER PUBLICATIONS

Interview Summary dated Jun. 28, 2012 in U.S. Appl. No. 11/944,027.
Final Office Action dated Oct. 22, 2012 in U.S. Appl. No. 11/944,027.
Notice of Allowance dated Jun. 5, 2013 in U.S. Appl. No. 11/944,027.
Interview Summary dated Jun. 7, 2011 in U.S. Appl. No. 11/944,000.
Appeal Brief dated Mar. 4, 2013 in U.S. Appl. No. 11/944,000.
Examiner's Answer dated Jun. 26, 2013 in U.S. Appl. No. 11/944,000.
Office Action dated Feb. 3, 2012 in U.S. Appl. No. 12/622,404.
Interview Summary dated May 8, 2012 in U.S. Appl. No. 12/622,404.
Final Office Action dated Aug. 6, 2012 in U.S. Appl. No. 12/622,404.
Notice of Allowance dated Oct. 15, 2012 in U.S. Appl. No. 12/622,404.
Office Action dated Mar. 4, 2013 in U.S. Appl. No. 12/891,543.
Interview Summary dated Apr. 5, 2013 in U.S. Appl. No. 12/891,543.
Mendelson, et al., "Informatics in Radiology—Image Exchange: IHE and the Evolution of Image Sharing," RadioGraphics, Nov.-Dec. 2008, vol. 28, No. 7.
Interview Summary dated Mar. 14, 2014, in U.S. Appl. No. 13/477,853.
Interview Summary dated Feb. 4, 2014, in U.S. Appl. No. 12/857,915.
Notice of Allowance, dated Jan. 9, 2014 in U.S. Appl. No. 13/345,606.
Non Final Office Action dated Aug. 23, 2013 in U.S. Appl. No. 13/907,128.
Final Office Action dated Oct. 9, 2013 in U.S. Appl. No. 13/907,128.
Interview Summary dated Nov. 22, 2013 in U.S. Appl. No. 13/907,128.
Notice of Allowance dated Jan. 31, 2014 in U.S. Appl. No. 13/907,128.
Office Action, dated Mar. 13, 2014 in U.S. Appl. No. 11/942,687.
Notice of Allowance dated Nov. 14, 2013 in U.S. Appl. No. 12/891,543.
U.S. Appl. No. 12/437,522, May 7, 2009, Fram.
U.S. Appl. No. 13/572,397, Aug. 10, 2012, Reicher.
U.S. Appl. No. 13/572,547, Aug. 10, 2012, Reicher.
U.S. Appl. No. 13/572,552, Aug. 10, 2012, Reicher.
Non-Final Office Action dated Aug. 28, 2007 in U.S. Appl. No. 11/179,384.
Final Office Action dated Jun. 26, 2008 in U.S. Appl. No. 11/179,384.
Non-Final Office Action dated Dec. 29, 2008 in U.S. Appl. No. 11/179,384.
Final Office Action dated Jul. 24, 2009, in U.S. Appl. No. 11/179,384.
Notice of Allowance dated Nov. 3, 2009, in U.S. Appl. No. 11/179,384.
Non-Final Office Action dated Aug. 18, 2010 in U.S. Appl. No. 12/702,976.
Interview Summary dated Dec. 1, 2010, in U.S. Appl. No. 12/702,976.
Final Office Action dated Feb. 17, 2011 in U.S. Appl. No. 12/702,976.
Final Office Action dated Jun. 13, 2014, in U.S. Appl. No. 13/477,853.
Notice of Allowance dated Aug. 15, 2014, in U.S. Appl. No. 13/477,853.
Interview Summary dated Jan. 25, 2010, in U.S. Appl. No. 11/268,261.
Notice of Allowance dated Oct. 8, 2010, in U.S. Appl. No. 11/268,261.
Notice of Allowance dated Dec. 3, 2010, in U.S. Appl. No. 11/268,261.
Notice of Allowance dated Jan. 6, 2011, in U.S. Appl. No. 11/268,261.
Notice of Allowance dated Jul. 3, 2014, in U.S. Appl. No. 12/857,915.
"Corrected" Notice of Allowance dated Aug. 15, 2014, in U.S. Appl. No. 12/857,915.
Non-Final Office Action dated May 13, 2009, in U.S. Appl. No. 11/265,979.
Final Office Action dated Dec. 22, 2009 in U.S. Appl. No. 11/265,979.
Non-Final Office Action dated Jul. 8, 2010 in U.S. Appl. No. 11/265,979.
Interview Summary dated Mar. 4, 2010 in U.S. Appl. No. 11/265,979.
Interview Summary dated Nov. 16, 2010 in U.S. Appl. No. 11/265,979.
Final Office Action dated Dec. 23, 2010 in U.S. Appl. No. 11/265,979.
Interview Summary dated Mar. 17, 2011 in U.S. Appl. No. 11/265,979.
Office Action dated Mar. 3, 2015 in U.S. Appl. No. 14/095,123.
Non-Final Office Action dated Aug. 24, 2009 in U.S. Appl. No. 11/268,262.
Non-Final Office Action dated Apr. 16, 2010 in U.S. Appl. No. 11/268,262.
Interview Summary dated Nov. 24, 2009 in U.S. Appl. No. 11/268,262.
Interview Summary dated May 12, 2010 in U.S. Appl. No. 11/268,262.
Final Office Action dated Oct. 28, 2010 in U.S. Appl. No. 11/268,262.
Interview Summary dated Dec. 1, 2010 in U.S. Appl. No. 11/268,262.
Notice of Allowance dated Dec. 1, 2010 in U.S. Appl. No. 11/268,262.
Notice of Allowance dated Feb. 25, 2011 in U.S. Appl. No. 11/268,262.
Non-Final Office Action dated Jul. 27, 2009 in U.S. Appl. No. 11/265,978.
Notice of Allowance dated Nov. 19, 2009 in U.S. Appl. No. 11/265,978.
Notice of Allowance dated Apr. 19, 2010 in U.S. Appl. No. 11/265,978.
Supplemental Notice of Allowance dated May 3, 2010 in U.S. Appl. No. 11/265,978.
Supplemental Notice of Allowance dated Aug. 3, 2010 in U.S. Appl. No. 11/265,978.
Non-Final Office Action dated May 26, 2010 in U.S. Appl. No. 11/942,674.
Interview Summary dated Jul. 26, 2010 in U.S. Appl. No. 11/942,674.
Final Office Action dated Nov. 26, 2010 in U.S. Appl. No. 11/942,674.
Interview Summary dated Mar. 2, 2011 in U.S. Appl. No. 11/942,674.
Notice of Allowance, dated Apr. 1, 2011 in U.S. Appl. No. 11/942,674.
Non Final Office Action dated Sep. 16, 2010 in U.S. Appl. No. 11/942,687.
Interview Summary dated Dec. 3, 2010 in U.S. Appl. No. 11/942,687.
Final Office Action, dated Apr. 5, 2011 in U.S. Appl. No. 11/942,687.
Interview Summary, dated Jun. 17, 2014 in U.S. Appl. No. 11/942,687.
Office Action, dated Jul. 18, 2014 in U.S. Appl. No. 11/942,687.
Interview Summary, dated Mar. 4, 2015 in U.S. Appl. No. 11/942,687.
Non-Final Office Action dated Apr. 14, 2010 in U.S. Appl. No. 11/944,027.

(56) References Cited

OTHER PUBLICATIONS

Interview Summary dated May 13, 2010 in U.S. Appl. No. 11/944,027.
Final Office Action dated Dec. 23, 2010 in U.S. Appl. No. 11/944,027.
Interview Summary dated Mar. 31, 2011 in U.S. Appl. No. 11/944,027.
Office Action dated Apr. 19, 2012 in U.S. Appl. No. 11/944,027.
Final Office Action dated Apr. 1, 2015 in U.S. Appl. No. 14/043,165.
Non-Final Office Action dated Sep. 29, 2010 in U.S. Appl. No. 11/944,000.
Final Office Action dated Apr. 20, 2011 in U.S. Appl. No. 11/944,000.
Office Action dated Mar. 17, 2015 in U.S. Appl. No. 13/768,765.
Office Action dated Sep. 11, 2014 in U.S. Appl. No. 14/179,328.
Notice of Allowance dated Jan. 14, 2015 in U.S. Appl. No. 14/179,328.
Office Action dated Jun. 27, 2014 in U.S. Appl. No. 13/572,397.
Final Office Action dated Jan. 13, 2015 in U.S. Appl. No. 13/572,397.
Notice of Allowance dated Mar. 19, 2015, 2015 in U.S. Appl. No. 13/572,397.
Office Action dated Aug. 6, 2014 in U.S. Appl. No. 13/572,547.
Notice of Allowance, dated Mar. 3, 2015 in U.S. Appl. No. 13/572,547.
Corrected Notice of Allowance, dated Apr. 10, 2015 in U.S. Appl. No. 13/572,547.
Office Action dated Jul. 30, 2014 in U.S. Appl. No. 13/572,552.
Interview Summary dated Sep. 3, 2014 in U.S. Appl. No. 13/572,552.
Final Office Action dated Jan. 28, 2105 in U.S. Appl. No. 13/572,552.
AGFA HealthCare, color brochure "IMPAX 6: Digital Image and Information Management," © 2012 Agfa HealthCare N.V. Downloaded from http://www.agfahealthcare.com/global/en/he/library/libraryopen?ID=32882925. Accessed on Feb. 9, 2015.
AGFA HealthCare, IMPAX 6.5 Datasheet (US)2012. © 2012 Agfa HealthCare N.V. Downloaded from http://www.agfahealthcare.com/global/en/he/library/libraryopen?ID=37459801. Accessed on Feb. 9, 2015.
AMD Technologies, Inc., Catella PACS 5.0 Viewer User Manual (112 pgs), © 2010, AMD Technologies, Inc. (Doc. 340-3-503 Rev. 01). Downloaded from http://www.amdtechnologies.com/lit/cat5viewer.pdf. Accessed on Feb. 9, 2015.
Aspyra's Imaging Solutions, 3 page color print out. Accessed at http://www.aspyra.com/imaging-solutions. Accessed on Feb. 9, 2015.
Avreo, interWorks—RIS/PACS package, 2 page color brochure, © 2014, Avreo, Inc. (Document MR-5032 Rev. 4). Downloaded from http://www.avreo.com/ProductBrochures/MR-5032Rev.%204interWORKS%20RISPACSPackage.pdf. Accessed on Feb. 9, 2015.
BRIT Systems, BRIT PACS View Viewer, 2 page color brochure, (BPB-BPV-0001). Downloaded from http://www.brit.com/pdfs/britpacsview.pdf. Accessed on Feb. 9, 2015.
BRIT Systems, Roentgen Works—100% Browers-based VNA (Vendor Neutral Archive/PACS), © 2010 BRIT Systems, 1 page color sheet. Accessed at http://www.roentgenworks.com/PACS. Accessed on Feb. 9, 2015.
BRIT Systems, Vision Multi-modality Viewer—with 3D, 2 page color brochure, (BPB-BVV-0001 REVC). Downloaded from http://www.brit.com/pdfs/BPB-BVV-0001REVC_BRIT_Vision_Viewer.pdf. Accessed on Feb. 9, 2015.
CANDELiS, ImageGrid™: Image Management Appliance, 6 page color brochure. (AD-012 Rev. F Nov. 2012), © 2012 Candelis, Inc. Downloaded from http://www.candelis.com/images/pdf/Candelis_ImageGrid_Appliance_20111121.pdf. Accessed on Feb. 9, 2015.
Carestream, Cardiology PACS, 8 page color brochure. (CAT 866 6075 Jun. 2012). © Carestream Health, Inc., 2012. Downloaded from http://www.carestream.com/cardioPACS_brochure_M1-877.pdf. Accessed on Feb. 9, 2015.
Carestream, Vue PACS, 8 page color brochure. (CAT 300 1035 May 2014). © Carestream Health, Inc., 2014. Downloaded from http://www.carestream.com/csPACS_brochure_M1-876.pdf. Accessed on Feb. 9, 2015.
Cerner, Radiology—Streamline image management, 2 page color brochure, (fl03_332_10_v3). Downloaded from http://www.cerner.com/uploadedFiles/Clinical_Imaging.pdf. Accessed on Feb. 9, 2015.
CoActiv, EXAM-PACS, 2 page color brochure, © 2014 CoActiv, LLC. Downloaded from http://coactiv.com/wp-content/uploads/2013/08/EXAM-PACS-BROCHURE-final-web.pdf. Accessed on Feb. 9, 2015.
Crowley, Rebecca et al., Development of Visual Diagnostic Expertise in Pathology: an Information-processing Study, Jan. 2003, Journal of the American medical Informatics Association, vol. 10, No. 1, pp. 39-51.
DR Systems, Dominator™ Guide for Reading Physicians, Release 8.2, 546 pages, (TCP-000260-A), © 1997-2009, DR Systems, Inc. Downloaded from https://resources.dominator.com/assets/004/6999.pdf. Document accessed Feb. 9, 2015.
DR Systems, DR Scheduler User Guide, Release 8.2, 410 pages, (TCP-000115-A), © 1997-2009, DR Systems, Inc. Downloaded from https://resources.dominator.com/assets/003/6850.pdf. Document accessed Feb. 9, 2015.
Erickson, et al.: "Effect of Automated Image Registration on Radiologist Interpretation," Journal of Digital Imaging, vol. 20, No. 2 Jun. 2007; pp. 105-113.
Erickson, et al.: "Image Registration Improves Confidence and Accuracy of Image Interpretation," Special Issue—Imaging Informatics, Cancer Informatics 2007: 1 19-24.
Fujifilm Medical Systems, SYNAPSE® Product Data, Synapse Release Version 3.2.1, Foundation Technologies, 4 page color brochure, (XBUSSY084) Aug. 2008. Downloaded from http://www.fujifilmusa.com/shared/bin/foundation.pdf. Accessed on Feb. 9, 2015.
Fujifilm Medical Systems, SYNAPSE® Product Data, Synapse Release Version 3.2.1, Server Modules and Interfaces, 4 page color brochure, (XBUSSY085) Aug. 2008. Downloaded from http://www.fujifilmusa.com/shared/bin/server-interface.pdf. Accessed on Feb. 9, 2015.
Fujifilm Medical Systems, SYNAPSE® Product Data, Synapse Release Version 3.2.1, Workstation Software, 4 page color brochure, (XBUSSY082) Aug. 2008. Downloaded from http://www.fujifilmusa.com/shared/bin/workstation.pdf. Accessed on Feb. 9, 2015.
GE Healthcare, Centricity PACS, in 8 page printout. Accessed at http://www3.gehealthcare.com/en/products/categories/healthcare_it/medical_imaging_informatics_-_ris-pacs-cvis/centricity_pacs. Accessed on Feb. 9, 2015.
Handylife.com—Overview of Handy Patients Enterprise, in 2 page printout. Accessed from http://www.handylife.com/en/software/overview.html. Accessed on Feb. 18, 2015.
Handylife.com—Features of Handy Patients Enterprise, in 4 page printout. Accessed from http://www.handylife.com/en/software/features.html. Accessed on Feb. 18, 2015.
Handylife.com—Screenshots of Handy Patients Enterprise, in 2 page printout. Accessed from http://www.handylife.com/en/software/screenshots.html. Accessed on Feb. 18, 2015.
iCRco, I See the Future, in 12 pages, color brochure, (BR080809AUS), © 2009 iCRco.ClarityPACS. Downloaded from http://www.claritypacs.com/pdfs/ISeeFuture_26_Web.pdf. Accessed on Feb. 9, 2015.
Imageanalysis, dynamika, 2 page color brochure. Downloaded from http://www.imageanalysis.org.uk/what-we-do. Accessed on Feb. 9, 2015.
Imageanalysis, MRI Software, in 5 page printout. Accessed at http://www.imageanalysis.org.uk/mri-software. Accessed on Feb. 9, 2015.

(56) References Cited

OTHER PUBLICATIONS

IMSI, Integrated Modular Systems, Inc., Hosted / Cloud PACS in one page printout. Accessed at http://www.imsimed.com/#!products-services/ctnu. Accessed on Feb. 9, 2015.

Infinitt, PACS, RIS, Mammo PACS, Cardiology Suite and 3D/Advanced Visualization | Infinittna, 2 page printout. Accessed at http://www.infinittna.com/products/radiology/radiology-pacs. Accessed on Feb. 9, 2015.

Intelerad, IntelePACS, 2 page color brochure, © 2014 Intelerad Medical Systems Incoprorated. Downloaded http://www.intelerad.com/wp-content/uploads/sites/2/2014/08/IntelePACS-brochure.pdf. Accessed on Feb. 9, 2015.

Intelerad, InteleViewer, 2 page color brochure, © 2014 Intelerad Medical Systems Incoprorated. Downloaded from http://www.intelerad.com/wp-content/uploads/sites/2/2014/09/InteleViewer-brochure.pdf. Accessed on Feb. 9, 2015.

Intuitive Imaging Informatics, ImageQube, 1 page in color. Downloaded from http://www.intuitiveimaging.com/2013/pdf/ImageQube%20one-sheet.pdf. Accessed on Feb. 9, 2015.

Kuhl, Helen: Comparison Chart/PACS, Customers Are Happy, But Looking for More, (color) Imaging Techology News, itnonline.com, May 2012, pp. 24-27. Downloaded from http://www.merge.com/MergeHealthcare/media/company/In%20The%20News/merge-pacs-comparison.pdf. Accessed on Feb. 9, 2015.

Lumedx CardioPACS 5.0 Web Viewer, Cardiopacs Module, 2 page color brochure, (506-10011 Rev A). Downloaded from http://cdn.medicexchange.com/images/whitepaper/cardiopacs_web_viewer.pdf?1295436926. Accessed on Feb. 9, 2015.

Lumedx Cardiovascular Information System, CardioPACS, one page in color printout. Accessed at http://www.lumedx..com/pacs.aspx. Accessed on Feb. 9, 2015.

McKesson Enterprise Medical Imagining and PACS | McKesson, 1 page (color) printout. Accessed at http://www.mckesson.com/providers/health-systems/diagnostic-imaging/enterprise-medical-imaging. Accessed on Feb. 9, 2015.

Medweb Radiology Workflow Solutions, Radiology Workflow Solutions, Complete Workflow & Flexible Turnkey Solutions, Web RIS/PACS with Advanced Viewer, 3 page color brochure, © 2006-2014 Medweb. Downloaded from http://www.medweb.com/docs/rispacs_brochure_2014.pdf. Accessed on Feb. 9, 2015.

Merge Radiology Solutions, Merge PACS, A real-time picture archiving communication system, (PAX-21990 rev 2.0), 2 page color brochure. Downloaded from http://www.merge.com/MergeHealthcare/media/documents/brochures/Merge_PACS_web.pdf. Accessed on Feb. 9, 2015.

Novarad Enterprise Imaging Solutions, NOVAPACS, 2 page (color) printout. Accessed at http://ww1.novarad.net/novapacs. Accessed on Feb. 9, 2015.

PACSPLUS, PACSPLUS Server, 1 page (color) printout. Accessed at http://www.pacsplus.com/01_products/products_01.html. Accessed on Feb. 9, 2015.

PACSPLUS, PACSPLUS Workstation, 3 page (color) printout. Accessed at http://www.pacsplus.com/01_products/products_01.html. Accessed on Feb. 9, 2015.

Philips IntelliSpace PACS, in 2 color page printout. Accessed at https://www.healthcare.philips.com/main/products/healthcare_informatics/products/enterprise_imaging_informatics/isite_pacs. Accessed on Feb. 9, 2015.

RamSoft, RIS PACS Teleradiology, PowerServer PACS, Lite PACS, XU PACS Compare RamSoft PACS Products, 2 color page printout. Accessed at http://www.ramsoft.com/products/powerserver-pacs-overview. Accessed on Feb. 9, 2015.

Sage Intergy PACS | Product Summary. Enhancing Your Workflow by Delivering Web-based Diagnostic Images When and Where You Need Them, in 2 color pages. (IRV-SS-INTPACS-PSS-031309). © 2009 Sage Software Healcare, Inc. Downloaded from http://www.greenwayhealth.com/solutions/intergy/. Accessed on Feb. 9, 2015.

Schellingerhout, Dawid, MD, et al.: "Coregistration of Head CT Comparison Studies: Assessment of Clinical Utility," Aced Radiol 2003; 10:242-248.

ScImage, Cardiology PACS, in 8 color page printout. Accessed at http://www.scimage.com/solutions/clinical-solutions/cardiology. Accessed on Feb. 9 2015.

Sectra RIS PACS, in 2 color page printout. Accessed at https://www.sectra.com/medical/diagnostic_imaging/solutions/ris-pacs/. Accessed on Feb. 9, 2015.

Siemens syngo.plaza, Features and Benefits, in 2 color page printout. Accessed at http://www.healthcare.siemens.com/medical-imaging-it/imaging-it-radiology-image-management-pacs/syngoplaza/features. Accessed on Feb. 9, 2015.

Simms | RIS and PACS Medical Imaging Software, in 2 color page printout. http://www.mysimms.com/ris-pacs.php. Accessed on Feb. 9, 2015.

Stryker, Imaging—OfficePACS Power Digital Imaging, in one color page printout. Accessed from http://www.stryker.com/emea/Solutions/Imaging/OfficePACSPowerDigitalImaging/index.htm. Accessed on Feb. 9, 2015.

Stryker, OfficePACS Power—Digital Imaging, 8 page color brochure, (MPP-022 Rev 4 BC/MP 300 1/07). © 2007 Stryker. Downloaded from http://www.stryker.com/emea/Solutions/Imaging/OfficePACSPowerDigitalImaging/ssLINK/emea/1557/022268. Accessed on Feb. 9, 2015.

UltraRAD—ultra Vision, 1 page (color). Downloaded from http://www.ultraradcorp.com/pdf/UltraVISION.pdf. Accessed on Feb. 9, 2015.

VioStream for VitreaView, 2 color pages printout. Accessed at http://www.vitalimages.com/solutions/universal-viewing/viostream-for-vitreaview. Accessed on Feb. 9, 2015.

Visage Imaging Visage 7, 3 color page printout. Accessed at http://www.visageimaging.com/visage-7. Accessed on Feb. 9, 2015.

Viztek Radiology PACS Software Vixtek Opal-RAD, 4 color page printout. Accessed at http://viztek.net/products/opal-rad. Accessed on Feb. 9, 2015.

Voyager Imaging—Voyager PACS Radiologist Workstation, 2 page color brochure. Downloaded from http://www.intellirad.com.au/assets/Uploads/Voyager-PacsWorkstations.pdf?. Accessed on Feb. 9, 2015.

Voyager Imaging—Voyager PACS, 3 page color brochure. Downloaded from http://www.intellirad.com.au/index.php/assets/Uploads/Voyager-Pacs3.pdf. Accessed on Feb. 9, 2015.

Ivetic, D., and Dragan, D., Medical Image on the Go!, 2009, J Med Syst, vol. 35, pp. 499-516.

Tahmoush, D. and Samet, H., A New Database for Medical Images and Information, 2007, Medical Imaging 2007; PACS and Imaging Informatics, vol. 6516. pp. 1-9.

U.S. Appl. No. 13/768,765, Systems and Method of Providing Dynamic and Customizable Medical Examination Forms, filed Feb. 15, 2013.

U.S. Appl. No. 14/540,830, filed Nov. 13, 2014 including its ongoing prosecution history, including without limitation Office Actions, Amendments, Remarks, and any other potentially relevant documents, Reicher et al.

U.S. Appl. No. 14/502,055, filed Sep. 30, 2014 including its ongoing prosecution history, including without limitation Office Actions, Amendments, Remarks, and any other potentially relevant documents, Fram et al.

U.S. Appl. No. 14/095,123, filed Dec. 3, 2013 including its ongoing prosecution history, including without limitation Office Actions, Amendments, Remarks, and any other potentially relevant documents, Reicher et al.

U.S. Appl. No. 14/081,225, filed Nov. 15, 2013 including its ongoing prosecution history, including without limitation Office Actions, Amendments, Remarks, and any other potentially relevant documents, Fram et al.

U.S. Appl. No. 14/244,431, filed Apr. 3, 2014 including its ongoing prosecution history, including without limitation Office Actions, Amendments, Remarks, and any other potentially relevant documents, Reicher et al.

U.S. Appl. No. 11/942687, filed Nov. 19, 2007 including its ongoing prosecution history, including without limitation Office Actions, Amendments, Remarks, and any other potentially relevant documents, Reicher, et al.

(56) References Cited

OTHER PUBLICATIONS

U.S. Appl. No. 14/043,165, filed Oct. 1, 2013 including its ongoing prosecution history, including without limitation Office Actions, Amendments, Remarks, and any other potentially relevant documents, Reicher, et al.
U.S. Appl. No. 11/944,000, filed Nov. 21, 2007 including its ongoing prosecution history, including without limitation Office Actions, Amendments, Remarks, and any other potentially relevant documents, Reicher, et al.
U.S. Appl. No. 13/768,765, filed Feb. 15, 2013 including its ongoing prosecution history, including without limitation Office Actions, Amendments, Remarks, and any other potentially relevant documents, Reicher et al.
U.S. Appl. No. 14/687,853, filed Apr. 15, 2015 including its ongoing prosecution history, including without limitation Office Actions, Amendments, Remarks, and any other potentially relevant documents, Reicher et al.
U.S. Appl. No. 14/792,210, filed Jul. 6, 2015 including its ongoing prosecution history, including without limitation Office Actions, Amendments, Remarks, and any other Potentially relevant documents, Reicher.
Office Action dated Dec. 11, 2013, in U.S. Appl. No. 13/477,853.
Non-Final Office Action dated Oct. 1, 2009, in U.S. Appl. No. 11/268,261.
Notice of Allowance dated Feb. 2, 2010, in U.S. Appl. No. 11/268,261.
Interview Summary dated May 1, 2015 in U.S. Appl. No. 14/095,123.
Final Office Action dated Jul. 23, 2015 in U.S. Appl. No. 14/095,123.
Interview Summary dated Aug. 27, 2015 in U.S. Appl. No. 14/095,123.
Office Action dated Oct. 14, 2014 in U.S. Appl. No. 14/043,165.
Office Action dated Oct. 2, 2015 in U.S. Appl. No. 14/043,165.
Interview Summary dated Jun. 11, 2015 in U.S. Appl. No. 13/768,765.
Notice of Allowance dated Aug. 28, 2015 in U.S. Appl. No. 13/768,765.
Corrected Notice of Allowance, dated May 21, 2015 in U.S. Appl. No. 13/572,547.
Interview Summary dated Apr. 23, 2015 in U.S. Appl. No. 13/572,552.
Notice of Allowance, dated May 8, 2015 in U.S. Appl. No. 13/572,552.
Philips, IntelliSpace: Multi-modality tumor tracking application versus manual PACS methods, A time study for Response Evaluation Criteria in Solid Tumors (RECIST). 2012, Koninklijke Philips Electronics N.V., in four pages.
Non-Final Office Action dated Jan. 20, 2016, in U.S. Appl. No. 14/502,055.
Interview Summary dated Apr. 14, 2016, in U.S. Appl. No. 14/502,055.
Office Action dated Feb. 23, 2016 in U.S. Appl. No. 14/095,123.
Office Action dated Mar. 10, 2016 in U.S. Appl. No. 14/081,225.
Non-Final Office Action dated Mar. 18, 2016 in U.S. Appl. No. 14/244,431.
Final Office Action, dated Jan. 5, 2015 in U.S. Appl. No. 11/942,687.
Notice of Appeal and Interview Summary, dated May 5, 2015 in U.S. Appl. No. 11/942,687.
PTAB Examiner's Answer, dated Feb. 25, 2016 in U.S. Appl. No. 11/942,687.
Interview Summary dated Dec. 21, 2015 in U.S. Appl. No. 14/043,165.
Final Office Action dated Feb. 17, 2016 in U.S. Appl. No. 14/043,165.
Board Decision dated Mar. 23, 2016 in U.S. Appl. No. 11/944,000.
Notice of Allowability dated Nov. 20, 2015 in U.S. Appl. No. 13/768,765.
Office Action dated Aug. 13, 2015 in U.S. Appl. No. 14/687,853.
Notice of Allowance dated Feb. 25, 2016 in U.S. Appl. No. 14/687,853.
Rosset et al.: "OsiriX: An Open-Source Software for Navigating in Multidimensional DICOM Images," Journal of digital Imaging, Sep. 2004, pp. 205-216.
U.S. Appl. No. 14/540,830, Systems and Methods for Viewing Medical Images, filed Nov. 13, 2014.
U.S. Appl. No. 14/502,055, Systems and Methods for Interleaving Series of Medical Images, filed Sep. 30, 2014.
U.S. Appl. No. 14/095,123, Systems and Methods for Retrieval of Medical Data, filed Dec. 3, 2013.
U.S. Appl. No. 14/081,225, Systems and Methods for Viewing Medical 3D Imaging Volumes, filed Nov. 15, 2013.
U.S. Appl. No. 14/244,431, Systems and Methods for Matching, Naming, and Displaying Medical Images, filed Apr. 3, 2014.
U.S. Appl. No. 11/942,687, Smart Forms, filed Nov. 19, 2007.
U.S. Appl. No. 14/043,165, Automated Document Filing, filed Oct. 1, 2013.
U.S. Appl. No. 11/944,000, Exam Scheduling With Customer Configured Notifications, filed Nov. 21, 2007.
U.S. Appl. No. 13/768,765, System and Method of Providing Dynamic and Customizable Medical Examination Forms, filed Feb. 15, 2013.
U.S. Appl. No. 14/687,853, Rules-Based Approach to Rendering Medical Imaging Data, filed Apr. 15, 2015.
U.S. Appl. No. 14/792,210, Dynamic Montage Reconstruction, filed Jul. 6, 2015.
Final Office Action dated May 15, 2017 in U.S. Appl. No. 14/540,830.
Notice of Allowance, dated Apr. 11, 2017 in U.S. Appl. No. 15/292,023.
Office Action dated Jun. 27, 2017 in U.S. Appl. No. 15/469,342.
Office Action dated Jun. 26, 2017 in U.S. Appl. No. 15/469,281.
Office Action dated Jun. 27, 2017 in U.S. Appl. No. 15/469,296.
U.S. Appl. No. 15/631,291, filed Jun. 23, 2017, Reicher et al.
U.S. Appl. No. 15/631,313, filed Jun. 23, 2017, Fram et al.
Office Action dated Jan. 17, 2017 in U.S. Appl. No. 14/540,830.
Interview Summary dated Mar. 24, 2017 in U.S. Appl. No. 14/540,830.
Notice of Allowance dated Jun. 2, 2016 in U.S. Appl. No. 14/502,055.
Notice of Corrected Allowability dated Jul. 14 2016, in U.S. Appl. No. 14/502,055.
Notice of Corrected Allowability dated Sep. 19, 2016, in U.S. Appl. No. 14/502,055.
Office Action dated Dec. 12, 2016 in U.S. Appl. No. 15/254,627.
U.S. Appl. No. 15/469,281, filed Mar. 24, 2017, Reicher et al.
U.S. Appl. No. 15/469,296, filed Mar. 24, 2017, Reicher et al.
U.S. Appl. No. 15/469,342, filed Mar. 24, 2017, Reicher et al.
Notice of Allowance dated Apr. 3, 2017 in U.S. Appl. No. 15/254,627.
Final Office Action dated Jul. 20, 2016 in U.S. Appl. No. 14/095,123.
Notice of Allowance dated Mar. 30, 2017 in U.S. Appl. No. 14/095,123.
Corrected Notice of Allowance dated Jun. 27, 2016, in U.S. Appl. No. 14/502,055.
Notice of Allowance dated Sep. 2, 2016 in U.S. Appl. No. 14/081,225.
Corrected Notice of Allowance dated Oct. 21, 2016 in U.S. Appl. No. 14/081,225.
Interview Summary dated Jun. 17, 2016 in U.S. Appl. No. 14/244,431.
Notice of Allowance dated Aug. 18, 2016 in U.S. Appl. No. 14/244,431.
Corrected Notice of Allowance dated Nov. 16, 2016 in U.S. Appl. No. 14/244,431.
Appeal Brief dated Jul. 15, 2016 in U.S. Appl. No. 14/043,165.
Examiner's Answer dated Nov. 14, 2016, in U.S. Appl. No. 14/043,165.
Office Action, dated Jul. 15, 2016 in U.S. Appl. No. 11/944,000.
Notice of Allowance, dated Jan. 30, 2017, in U.S. Appl. No. 11/944,000.

(56) References Cited

OTHER PUBLICATIONS

Notice of Allowability dated Jul. 28, 2016 in U.S. Appl. No. 13/768,765.
Supplemental Notice of Allowance dated Jun. 2, 2016 in U.S. Appl. No. 14/687,853.
Notice of Allowance dated Aug. 11, 2016 in U.S. Appl. No. 15/163,600.
Supplemental Notice of Allowance dated Sep. 14, 2016 in U.S. Appl. No. 15/163,600.
Office Action, dated Jan. 12, 2017 in U.S. Appl. No. 15/292,023.
Restriction Requirement, dated Jul. 28, 2015 in U.S. Appl. No. 14/139,068.
Office Action, dated Mar. 11, 2016 in U.S. Appl. No. 14/139,068.
Notice of Allowance, dated Sep. 21, 2016 in U.S. Appl. No. 14/139,068.
Sandberg, et al., "Automatic detection and notification of "wrong paitent-wrong location" errors in the operating room," Surgical Innovation, vol. 12, No. 3, Sep. 2005, pp. 253-260.
Sprawls, "Image Characteristics and Quality," Physical Principles of Medical Imaging, http://www.sprawls.org/resources pp. 1-14.
TeraRecon iNtuition pamphlet in 20 pages, retrieved on Nov. 8, 2013, available at http://int.terarecon.com/wp-content/uploads/2013/11/brochure_english2013.pdf.
TeraRecon iNtuition — Workflow. <www.terarecon.com/wordpress/our-solutions/intuition-workflow> Last accessed Nov. 8, 2013, 2 pages.

\* cited by examiner

Exam Receive Options-IHS Central Server                                                                    [X]

☑ Schedule an automatic receive every [5 ⇕] minutes                          [ OK ]
☐ Receive exams upon login                                                    [ Cancel ]

302 ⎨ ┌─ Exam Copy Parameters ─────────────────────────────────────────┐
     │  ┌─ Exam Components ─────────────────────────────────────────┐  │
     │  │  ☑ Images   ☑ Montages   ☑ Voice Clips   ☑ Notes   ☐ Reports │  │
     │  └───────────────────────────────────────────────────────────┘  │
     └───────────────────────────────────────────────────────────────┘

┌─ Receivable Exam Criteria ────────────────────────────────────────────┐
│  ☐ I am the Assigned Reading Physician                                │
│  ☐ [ Modality... ]      [                                          ]  │
│  ☐ [ Acquisition Site...] [                                        ]  │
│  ☑ [ Exam Status... ]   [ Unread                                   ]  │
│  ☐ [ Exam Priority... ] [                                          ]  │
│  ☐ Additional Filter    [                             ▼]              │
│  ☑ Ignore exams older than  [ 2 weeks ▼]                              │
│  ☐ Ignore exams performed from [7:00.00 AM ⇕] to [11:00.00 PM ⇕]      │
│                                                                       │
│  Maximum number of [3] exam(s) will be received automatically. (Doesn't apply to manual receive) │
└───────────────────────────────────────────────────────────────────────┘

┌─ After Exams Received ────────────────────────────────────────────────┐
│  ☑ Play sound [1 ⇕] Times   [                              ▶] Browse  │
│  ☐ Launch program           [                              ▶] Browse  │
└───────────────────────────────────────────────────────────────────────┘

┌─310                          ┌─315
305 ⎨ [Copy Report to EMR] [Location:] [                    ] [▶ Browse]
     [Copy Montage > EMR] [Location:] [                    ] [▶ Browse]
                    └─320                          └─325
     [File Format]    ☐ [HL-7 Text]   ☐ [PDF]    ☐ [other...]
          └─330         └─332            └─334        └─336

SMART PLACEMENT RULES

CROSS-REFERENCE TO RELATED APPLICATIONS

This application is a continuation of U.S. application Ser. No. 13/907,128, filed May 31, 2013, titled "SMART PLACEMENT RULES," which is a continuation of U.S. application Ser. No. 13/118,085, filed May 27, 2011, titled "SMART PLACEMENT RULES," now U.S. Pat. No. 8,457,990, which is a continuation of U.S. application Ser. No. 11/942,674, filed Nov. 19, 2007, titled "SMART PLACEMENT RULES," now U.S. Pat. No. 7,953,614, which claims priority under 35 U.S.C. §119(e) to U.S. Provisional Application No. 60/867,071, filed Nov. 22, 2006. All of the above-identified applications are hereby incorporated by reference herein in their entireties.

BACKGROUND OF THE INVENTION

Field of the Invention

The invention relates to the management and placement of medical data, and more particularly to the smart placement of received medical data within an Electronic Medical Records (EMR) system, for example.

Description of the Related Art

Medical data is increasingly being stored in the form of digital documents that can be electronically transmitted and shared between multiple computing devices. EMR systems store various types of medical data, such as images from x-rays and MRIs, montages of images, voice clips, notes, reports, and other text, audio, and/or video from a wide variety of sources. EMR systems receive medical data from physicians or other medical practitioners, for example, that have generated and/or received the medical data from one or more imaging facilities. This medical data often needs to be viewed, manipulated, interpreted, and/or shared between multiple medical members in the same facility or members in one or more distant facility. Accordingly, there is a need for improved systems and methods for the smart placement of medical records so that collaboration among medical faculty can take place.

SUMMARY OF THE INVENTION

In one embodiment, a method of managing medical data received from at least one medical imaging facility, the medical data comprising medical images and medical reports, comprises receiving data from a user indicating a first storage location of an EMR system for storing medical images and a second storage location of the EMR system for storing medical reports received from the imaging facilities, receiving medical images and medical reports from at least one of the medical imaging facilities via one or more networks, associating each of the received medical images and medical reports with respective patients, and transferring the medical images and the medical reports to the EMR system with information indicating the first and second storage locations for the respective medical images and medical reports.

In one embodiment, a method of manipulating medical data associated with a patient comprises receiving first information from a user of a first computer specifying medical data to be retrieved by the first computer, receiving instructions comprising an indication of a secondary storage location, receiving medical data associated with a patient in response to matching the first information to certain attributes associated with the medical data, and transferring at least some of the medical data to the secondary storage location, wherein the secondary storage location is configured to associate the transferred medical data with other medical data associated with the patient so that the transferred medical data is accessible by users of the secondary storage system.

In one embodiment, a medical data management system comprises a storage device for storing received medical data associated with a patient and for storing smart placement rules indicating one or more components of medical data to be transferred to an indicated secondary storage location, and a smart placement module for identifying one or more components of the received medical data that are indicated in the smart placement rules and forwarding a copy of the identified one or more components to the secondary storage location.

In one embodiment, a method of forwarding medical data to a patient records system, the method comprises receiving rules from a user of a computing system, the rules comprising criteria indicating which components of the medical data should be transmitted from a medical image storage device to the computing system and/or when the components should be transmitted to the computing system, receiving a storage location from the user of the computing system indicating where the medical data is to be stored in a patient records system, attaching information to medical data received from the medical image storage device, the information indicating one or more storage locations in the patient record system so that respective storage locations are associated with different components of the received medical data, and transmitting the received medical data and the attached information to the patient records system.

BRIEF DESCRIPTION OF THE DRAWINGS

FIG. 3 is one embodiment of a graphical user interface that may be used to establish smart placement rules.

DETAILED DESCRIPTION OF THE CERTAIN EMBODIMENTS

Embodiments of the invention will now be described with reference to the accompanying figures, wherein like numerals refer to like elements throughout. The terminology used in the description presented herein is not intended to be interpreted in any limited or restrictive manner, simply because it is being utilized in conjunction with a detailed description of certain specific embodiments of the invention. Furthermore, embodiments of the invention may include several novel features, no single one of which is solely responsible for its desirable attributes or which is essential to practicing the inventions herein described.

As used herein, the terms "medical data," "medical-related data," and "medical records" are defined to include data in any format that is related to a patient. As non-limiting examples, the terms may include, but are not limited to, medical images, such as radiograph, computed tomography (CT), magnetic resonance imaging (MRI), Ultrasound (US), mammogram, positron emission tomography scan (PET), and nuclear scan (NM) images; montages of medical images; medical reports; voice clips, notes; and medical reports. Medical data may be stored in various formats, such as PDF, JPEG, GIF, PNG, DOC, XLS, PPT, MP3, WAV, HTML, XML, and various other formats.

A "component" of medical data is a category or type of medical data. For example, components of medical data may include an image component comprising medical images and a report component comprising a written report corresponding to the medical images. Components of medical data may include, for example, images, montages, voice clips, notes, and reports.

Figure 1A:
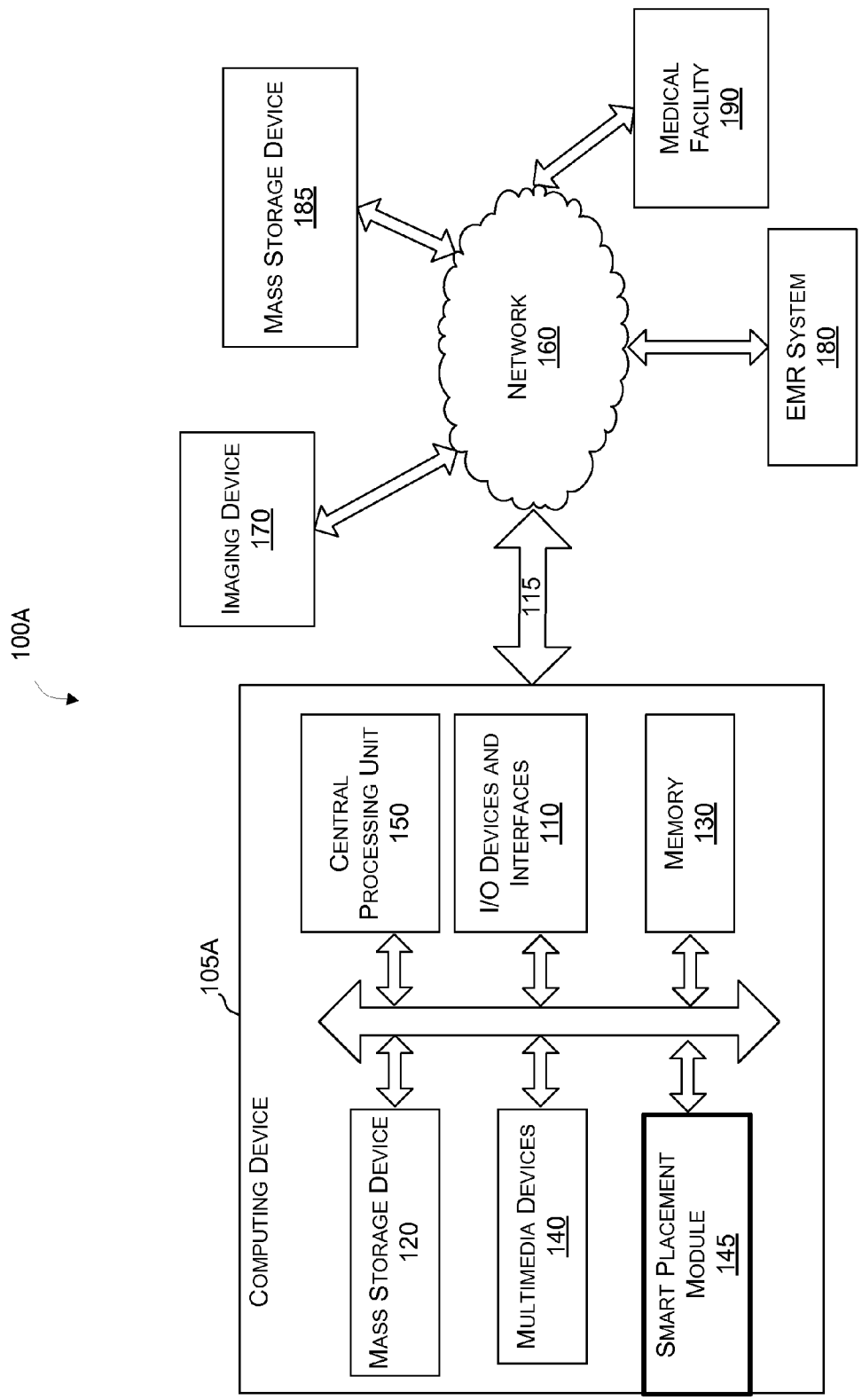
FIG. 1A is a block diagram of a computing system comprising a computing device in communication with a network and various networked devices.

FIG. 1A is a block diagram of a computing system 100A comprising a computing device 105A in communication with a network 160 and various networked devices. The computing system 100A may be used to implement certain systems and methods described herein. Depending on the embodiment, the functionality described below with reference to certain components and modules of the computing system 100A may be combined into fewer components and modules or further separated into additional components or modules.

The exemplary computing device 105 comprises a memory 130, such as random access memory ("RAM") for temporary storage of information and a read only memory ("ROM") for permanent storage of information, and a mass storage device 120, such as a hard drive, diskette, or optical media storage device. The mass storage device 120 may comprise one or more hard disk drive, optical drive, networked drive, or some combination of various digital storage systems. The computing device 105 also comprises a central processing unit (CPU) 150 for computation. Typically, the modules of the computing device 105 are in data communication via one or more standards-based bus system. In different embodiments of the present invention, the standards based bus system could be Peripheral Component Interconnect (PCI), Microchannel, SCSI, Industrial Standard Architecture (ISA) and Extended ISA (EISA) architectures, for example.

The computing device 105 is generally controlled and coordinated by operating system software, such as the Windows 95, 98, NT, 2000, XP, Vista, or other compatible operating systems. In Macintosh systems, the operating system may be any available operating system, such as Mac OS X. In other embodiments, the computing device 105 may be controlled by a proprietary operating system. Conventional operating systems control and schedule computer processes for execution, perform memory management, provide file system, networking, and I/O services, and provide a user interface, such as a graphical user interface ("GUI"), among other things.

The exemplary computing device 105A includes one or more of commonly available input/output (I/O) devices and interfaces 110, such as a keyboard, mouse, touchpad, and printer. In one embodiment, the I/O devices and interfaces 110 include one or more display devices, such as a monitor, that allows the visual presentation of data to a user. More particularly, display devices provide for the presentation of GUIs, application software data, and multimedia presentations, for example. According to the systems and methods described below, medical images may be stored on the computing device 105A and automatically transmitted to one or more EMR systems manipulated by the smart placement module 145 based on one or more placement rules established by a user of the computing device 105A. The computing device 105 may also include one or more multimedia devices 140, such as speakers, video cards, graphics accelerators, and microphones, for example.

In the embodiment of FIG. 1A, the I/O devices and interfaces 110 provide a communication interface to various external devices. In the embodiment of FIG. 1A, the computing device 105A is in data communication with a network 160, such as a LAN, WAN, or the Internet, for example, via a communication link 115. The network 160 may be coupled to various computing devices and/or other electronic devices. In the exemplary embodiment of FIG. 1A, the network 160 is in data communication with an imaging device 170, an Electronic Medical Record (EMR) system 180, a mass storage device 185, and a medical facility 190. Depending on the embodiment, the EMR system 180 may comprise proprietary medical record management software and/or one or more of various available third-party EMR systems. In addition to the devices that are illustrated in FIG. 1A, the network 160 may facilitate communications with other computing, imaging, and storage devices.

The imaging device 170 may be any type of device that is capable of acquiring medical images, such as MRI, x-ray, mammography, or CT scan systems. In one embodiment, the imaging device 170 is configured to store images and data associated with images. In one embodiment, the imaging device 170 communicates with the computing device 105 via the network 160, or one or more other wired and/or wireless networks, such as a secure LAN, for example. In one embodiment, the image data is stored in Digital Imaging and Communications in Medicine ("DICOM") format. The complete DICOM specifications, which may be found on the National Electrical Manufactures Association Website at <medical.nema.org>. Also, NEMA PS 3—*Digital Imaging and Communications in Medicine,* 2004 ed., Global Engineering Documents, Englewood Colo., 2004, is hereby incorporated by reference in its entirety.

The exemplary EMR system 180 is configured to store digital medical data so that doctors, medical staff, patients, and/or other authorized personnel can effectively view and share the medical data. The EMR system 180 may provide medical data from multiple sources to the computing device 105 via the network 160. Likewise, medical data from the computing device 105 may be provided to other medical facilities, such as the medical facility 190 of FIG. 1A, via the EMR system 180. Depending on the embodiment, the medical facility 190 may include one or more hospitals, clinics, doctor's offices, or any other facility that generates and/or processes medical data. The medical facility 190 may include one or more imaging devices, such as imaging devices that generate the image types described above in the definition of medical data. In one embodiment, multiple computing devices, such as the computing device 105, may be housed at the medical facility 190.

In the embodiment of FIG. 1A, the smart placement module 145 is configured to forward medical data received by the computing device 105A, such as from the imaging device 170 or the medical facility 190, to one or more EMR systems according to placement rules established by a user of the computing device 105. In one embodiment, medical data is received at the computing device 105 in response to matching of one or more auto-pull rules with particular medical data and/or components of the medical data. For example, in an auto-pull system, either the computing device 105 or a remote server may be configured to periodically select, based upon a user-defined schedule, medical data satisfying the user-specific rules. The user may be authenticated with the remote server in order to determine the user's rights to receive medical data and the selected medical data may then be transmitted to the computing device 105A so that it is locally available for the viewing physician, technician, or other authorized viewer. U.S. Pub. No. 2006/0095423, published on May 4, 2006 to Reicher et al. titled "Systems and Methods for Retrieval of Medical Data," which is hereby incorporated by reference in its entirety, describes various systems and methods for establishing auto-pull rules for selectively transferring medical data to a computing device.

In one embodiment, the smart placement module 145 determines components of received medical data to forward to one or more secondary storage locations, such as the EMR system 180 or a specific directory of a local storage device, based on smart placement rules that are established by an authorized user of the computing device 105. Although the description below refers primarily to an EMR system 180 as the secondary storage device, the systems and methods described herein are operable with any suitable secondary storage device, whether local or remote to the computing device 105.

Through the automatic application of smart placement rules by the smart placement module 145, the need for a user of the computing device 105 to manually select and transfer components of medical data to one or more secondary locations, such as the EMR system 180, is reduced or removed. Accordingly, the smart placement module 145 allows a user of the computing device 105, and other authorized computer users that are in communication with the EMR system 180, to locate data regarding a patient in the EMR system 180. In one embodiment, the smart placement module 145 provides an interface for an authorized user to establish smart placement rules that indicate what components of medical data should be forwarded to one or more secondary storage locations. In one embodiment, smart placement rules may also indicate storage locations for respective components of medical data, such as a directory on a local storage device, a directory on a shared storage device, or a folder in an EMR system, for example. Depending on the embodiment, the smart placement module 145 may be configured to copy the selected components of medical data (e.g., leaving a copy on the computing device 105) or to move the selected components of medical data (e.g., not leaving a copy on the computing device 105) to the selected secondary storage location. In one embodiment, the mass storage device 120 stores the user-specific rules. A further description of the smart placement module 145 and its processes will be discussed below.

Figure 1B:
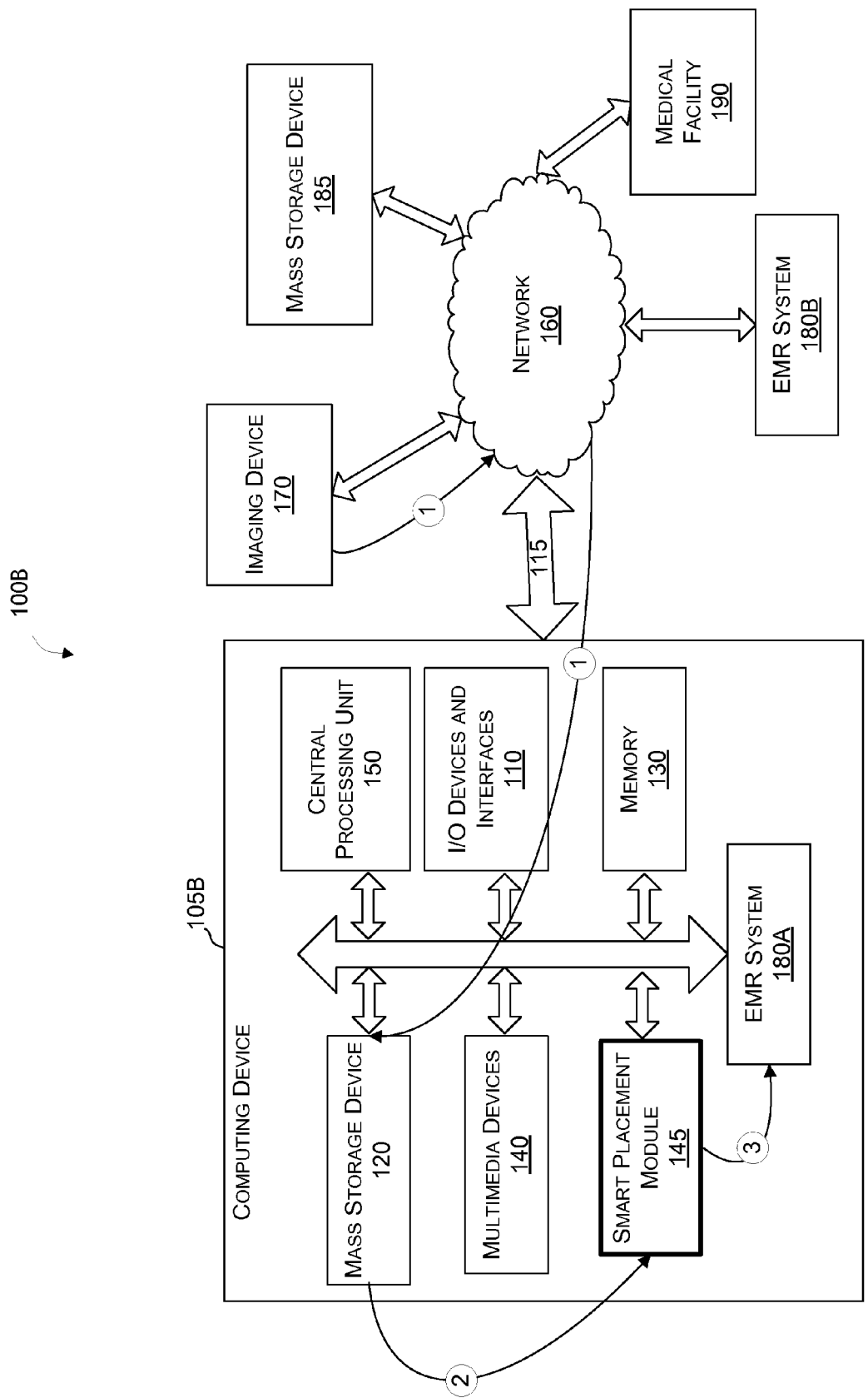
FIG. 1B is a block diagram illustrating one embodiment of a computing system comprising a computing device in communication with the imaging device via the network.

FIG. 1B is a block diagram illustrating one embodiment of a computing system 100B comprising a computing device 105B in communication with the imaging device 170 via the network 160. In the embodiment of FIG. 1B, the computing device 105B comprises a local version of the EMR system 180. In this embodiment, the EMR system 180 may be used exclusively by the computing device 105B, may be used by other devices coupled to the computing device 105B, such as via a secured local area network, and/or may be accessed by any authorized devices that are in communication with the network 160.

In the embodiment of FIG. 1B, an exemplary temporal flow of data is indicated by the circled numerals 1-3 and is described in further detail below. Depending on the embodiment, certain steps may be removed and additional steps may be added.

In step one of FIG. 1B, the imaging device 170 transmits medical data to the network 160, and the medical data, such as medical images, reports, and/or other medical information, is received and stored by the computing device 105B. In one embodiment, medical data is selected for transmission to the computing device 105B as a result of matching one or more auto-pull rules that are established by a user of the computing device 105B.

In step two, the smart placement module 145 of the computing device 105B applies smart placement rules to the received medical data. In one embodiment, the smart placement rules indicate that certain components of medical data is to be copied and/or moved to a secondary storage location either on the computing device 105B, such as in a folder of the EMR system 180, or to another device across the network 160. For example, smart placement rules may indicate that received medical data is to be transferred to a selected EMR system and associated with respective patient data on the EMR system.

In one embodiment, the smart placement rules indicate one or more components of medical data that are to be transmitted to a selected one or more destinations. For example, a user can establish placement rules indicating that only textual reports are to be transmitted to a selected EMR system, or the user can establish placement rules indicating that all components of received medical data should be transmitted to the selected EMR.

In step three of FIG. 1B, the indicated components of the received medical data are transmitted to the EMR system 180. In one embodiment, the transmitted components are associated with other medical data of the respective patient(s) at the EMR system 180. In such an embodiment, an authorized user of the EMR system 180 may access the transmitted components via the respective patient's inbox in the EMR system 180. Thus, in one embodiment the smart placement module 145 advantageously automates a process of selecting medical data for transmission to the EMR system 180 so that the medical data may be associated with other medical data associated with the patient at the EMR system 180. Additionally, the smart placement module 145 may be configured to automatically apply smart placement rules when medical data is received at the computing device 105 so that components of the medical data are quickly availably to authorized users of the EMR system, without any intervention by the user.

In one embodiment, the smart placement module 145 generates a token comprising information indicating one or more software applications associated with components of medical data that are transmitted to the EMR system 180. In one embodiment, the smart placement module 145 determines the appropriate text, graphic, audio, etc., viewer(s) that may be used to present respective data items that are transmitted to the EMR system 180. For example, if the retrieved medical data includes image files, then the token sent by the smart placement module 145 to the EMR system 180 may indicate a specific third-party software viewing application that the viewing system should launch in order to view the image files. In one embodiment, the tokens may designate a class of software application so that the user's default application of a given type of application may be selected when indicated by a token.

In one embodiment, the smart placement module 145 generates a patient ID file that is transmitted with the indicated components to the EMR system 180. The patient ID file comprises an indication of a patient name, examination date, medical record number, and/or social security number, for example, of a patient associated with the transmitted medical data components. Thus, the patient ID file is usable by the EMR system 180 to place the medical data components in locations associated with the appropriate patient, such as folders, directories, or inboxes associated with respective patients. In other embodiments, the patient ID file may comprise additional information regarding a patient.

Figure 2:
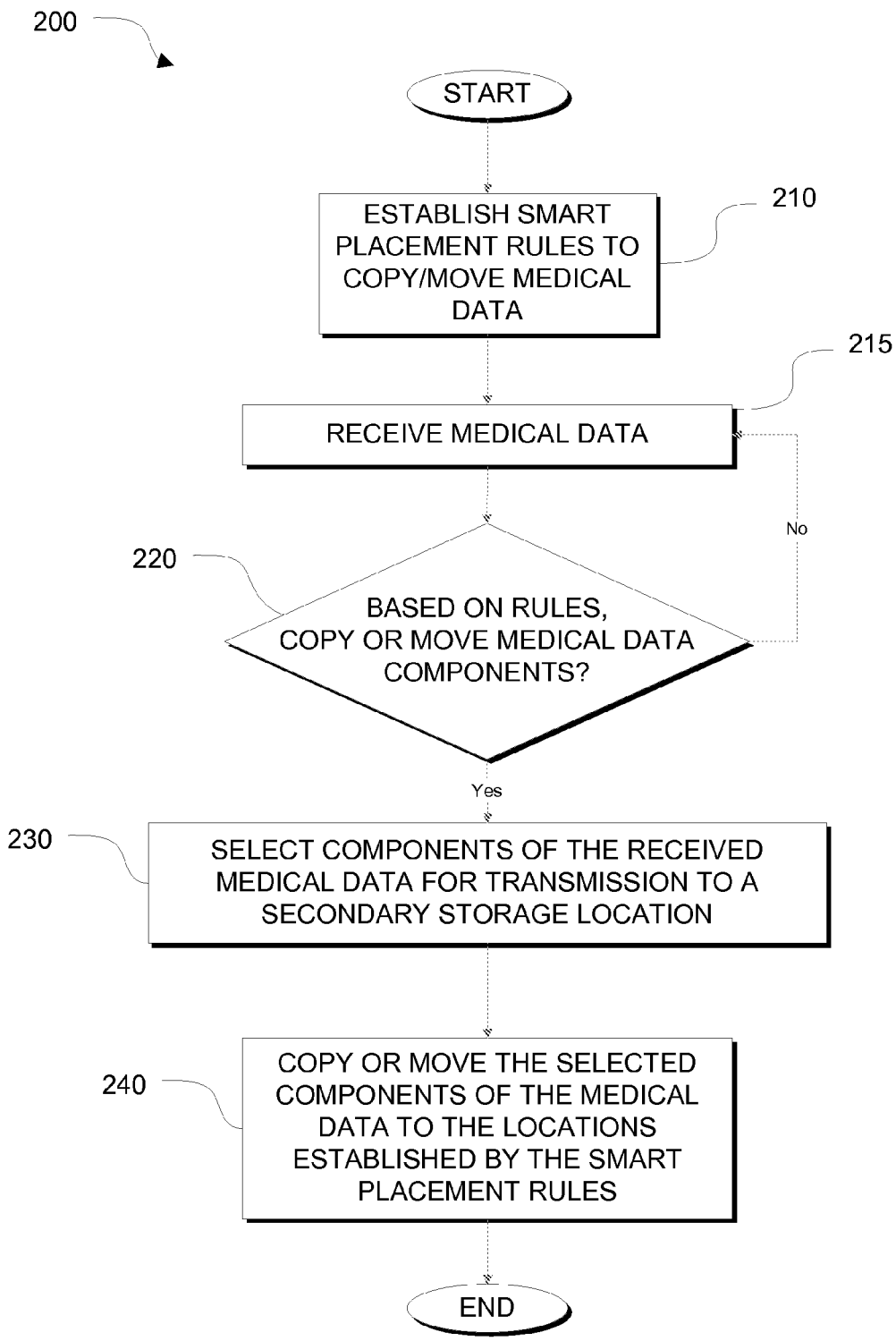
FIG. 2 is a flowchart illustrating one embodiment of a method of automatically forwarding received medical data to one or more predetermined locations based on smart placement rules.

FIG. 2 is a flowchart 200 illustrating one embodiment of a method of automatically forwarding received medical data to one or more predetermined locations based on smart placement rules. The method of FIG. 2A may be initiated in response to receiving new medical data at the computing device 105, such that the medical data is forwarded based on the smart placement rules substantially immediately after being received at the computing device 105. In other embodiments, the method of FIG. 2A is user initiated and may operate on medical data that has been stored on the computing devices or a networked device for an extended period of time. Depending on the embodiment, the flowchart of FIG. 2 may comprise fewer or more blocks and the blocks may be performed in a different order than illustrated.

Beginning in block 210, smart placement rules are established for movement or copying of medical data components to one or more secondary storage locations. In one embodiment, the smart placement rules comprise default system rules and/or user-specific rules for each user or group of users. Depending on the embodiment, the smart placement rules may include component criteria that must be matched by received medical data in order to trigger an associated smart placement action. For example, a smart placement rule may specify that only an image and report component of medical data is to be transmitted to a particular EMR system. Thus, when new medical data is received, only the image and report components are transmitted to the EMR system. In one embodiment, the smart placement rules indicated separate storage locations for respective medical data components, such as a first location for medical images and a second location for reports. Additionally, in some embodiments, the smart placement rules indicate a format that medical data components should be in prior to transferring to the EMR system, such as HL-7 text format, or PDF format, for example.

In one embodiment, the smart placement rules may also include criteria associated with header data of certain medical data components, such as time of day and/or date that a component is received by the computing device 105, a referring physician's name, a radiologist name, an exam type, an exam modality, and various other attributes of a components. In one embodiment, default system rules are applied to received medical data if user-specific rules have not been established. FIG. 3, which is described in further detail below, illustrates an exemplary user interfaces for establishing smart placement rules.

Moving to block 215, medical data is received at the computing device 105. As noted above, the medical data may be received from any suitable computing device that is in communication with the computing device 105, such as via the network 160. As defined above, the medical data may comprise one or more of multiple files of various formats and may include various information regarding a patient. In one embodiment, the medical data is stored in the mass storage system 120 of the computing device 105.

Next, in decision block 220 the computing device 105 applies the smart placement rules to the received medical data in order to determine which components of the medical data, if any, should be copied and/or moved to one or more local or remote secondary storage locations. If a smart placement rule matches one or more components of the medical data, the method continues to block 230. If no smart placement rules match with the medical data, the method returns to block 210 where medical data from another exam, another imaging source, and/or associated with another patient is received.

At block 230, the components of the medical data indicated by the placement rules are selected for transmission to the location indicated in the matching smart placement rule. As noted above, all components may be transmitted to a single location, e.g., a folder on a local or networked storage device or a local or networked EMR system, or the smart placement rules may indicate separate storage locations for respective components of the medical data.

Moving to block 240, the computing device 105 transmits the selected components to the location or locations associated with the matched smart placement rules. As noted above, in one embodiment a patient ID file indicating one or more attributes of the patient associated with the medical data components is also transmitted to the indicated secondary location. The patient ID file may be used, for example, by the EMR system in associating the transmitted medical data components with other medical data of respective patients. In this embodiment, the medical data of the patient is quickly made available to authorized users of the EMR system by accessing the patient's records stored by the EMR system.

In one embodiment, the smart placement module 145 generates one or more tokens that are associated with specific components of the transmitted medical data. The tokens comprise information regarding compatible and/or preferred software applications that may be launched in order to view and/or hear an associated medical data component. For example, if the selected medical data comprises a series of CT scan images, a token may be generated to indicate one or more software applications in which the CT images may be viewed. Likewise, a token indicating one or more software application in which a textual report may be viewed may be associated with a textual report component. In one embodiment, the EMR system 180 may display a link and/or icon associated with a token that may be selected by a user of the EMR system 180 in order to access the corresponding medical data in an appropriate software application. Certain tokens may comprise executable software code that launches a desired software application and opens selected medical data components in the software application. For example, an authorized user of the EMR system 180, such as a user of the computing device 105 or another computing device in communication with the network, may select a link associated with a token in order to invoke execution of the token, and subsequent launching of an indicated software application and opening of the corresponding medical data.

In one embodiment, the EMR system comprises separate patient inboxes wherein some or all of the patient's medical records are stored. In general, a patient's inbox is a location and/or index of locations where the patient's medical data is stored. This method may increase privacy of the medical data for specific patients by only allowing the patient, the patient's doctor, and/or other authorized users to access the patient's medical data.

FIG. 3 is one embodiment of a graphical user interface 300 that may be used to establish smart placement rules. Depending on the embodiment, the layout of the graphical user interface, the types of input fields, buttons, and checkboxes may be modified. The exemplary graphical user interface 300 comprises a component selection pane 302 that allows a user of the computing device 105, for example, to indicate which components of received medical data should be forwarded to one or more indicated secondary storage locations. In the embodiment of FIG. 3, check boxes for component types images, montages, voice clips, notes, and reports are provided, where a particular component is selected for transferring to an indicated secondary location if the corresponding checkbox is selected. In other embodiments, other controls may be used in order to allow a user to select one or more components. In other embodiments, fewer or additional components may be available for selection.

The exemplary user interface of FIG. 3 also comprises smart placement pane 305 that allow a user to select secondary storage locations for report and/or montage components of medical data. In the embodiment of FIG. 3, the smart placement pane 305 comprises a report copy button 310 that may be selected to indicate that received medical reports should be automatically transmitted to an EMR system, or other storage location, identified in field 315. Similarly, a montage copy button 320 may be selected in order to indicate that received montages should be automatically transmitted to an EMR system, or other storage location, identified in field 325.

In one embodiment, the smart placement module detects an EMR system that is used by the computing device and automatically populates fields 315, 325 with an indication of the detected EMR system(s). Where multiple EMR systems are detected, the text display fields 315, 325 may comprise drop-down fields that allow the user to select one or more of the EMR systems to which the medical data should be transmitted. In one embodiment, the user is provided with a directory structure that may be navigated in order to locate and select an EMR system or another storage location. In one embodiment, after establishing the smart placement rules, such as using the interface of FIG. 3, when medical data is received by the computing device 105, the components of the medical data indicated in the component selection pane 302 are automatically forward to the locations indicated in the smart placement pane 305.

The exemplary smart placement pane 305 further comprises buttons 332, 334, and 336 that allow the user to select a desired format for the medical data that is transmitted to the indicated EMR system. In the embodiment of FIG. 3A, HL-7 text format may be selected by selecting button 332 and PDF format may be selected by selecting button 334. In one embodiment, when button 332 is selected, medical data is converted into the Health Level 7 standard format, which is a widely known standard and format for medical records, before transmitting to the selected EMR system. Similarly, when button 334 is selected, medical data is converted into one or more Adobe PDFs before transmitting to the selected EMR system. The smart placement pane 305 further comprises another button 336 that allows the user to select other formats for the medical data. In one embodiment, when the button 336 is selected, another user interface comprising additional data formats, such as DOC or RTF, for example, is presented to the user.

The foregoing description details certain embodiments of the invention. It will be appreciated, however, that no matter how detailed the foregoing appears in text, the invention can be practiced in many ways. For example, the above-described auto-retrieve may be performed on other types of images, in addition to medical images. For example, images of circuit boards, airplane wings, and satellite imagery may be analyzed using the described systems. As is also stated above, it should be noted that the use of particular terminology when describing certain features or aspects of the invention should not be taken to imply that the terminology is being re-defined herein to be restricted to including any specific characteristics of the features or aspects of the invention with which that terminology is associated. The scope of the invention should therefore be construed in accordance with the appended claims and any equivalents thereof.

What is claimed is:

1. A method of distributing images over a network to a remote computing device, the method comprising:
    storing, at an image server comprising a microprocessor and a memory, user preferences of a user, wherein the user preferences include indications of an exam modality, an exam status, an image format, a software application, a transmission schedule, a first storage location, and a second storage location;
    receiving, at the image server and from an imaging device over a network, an imaging exam comprising a plurality of images;
    receiving, at the image server, a report;
    associating, by the microprocessor of image server, the report with the imaging exam;
    determining, by the microprocessor of the image server, that a modality of the imaging exam matches the exam modality indicated by the user preferences;
    determining, by the microprocessor of the image server, that a status of the imaging exam matches the exam status indicated by the user preferences;
    generating, by the microprocessor of the image server, an electronic token comprising executable software code, wherein the electronic token includes an indication of the software application indicated by the user preferences;
    associating, by the microprocessor of the image server, the electronic token with the imaging exam;
    in response to determining that a format of at least one image of the plurality of images of the imaging exam is not in the image format indicated by the user preferences, formatting, by the microprocessor of the image server, the at least one image to match the image format indicated by the user preferences;
    transmitting, by the image server, the report associated with the imaging exam from the image server to a first remote computing device based on the transmission schedule indicated by the user preferences;
    transmitting, by the image server, at least some of the plurality of images of the imaging exam and the electronic token from the image server to a second remote computing device when the second remote computing device is connected to the image server and based on the transmission schedule indicated by the user preferences;
    automatically generating and transmitting, by the image server and over the network, a notification to the user when the at least some of the plurality of images of the imaging exam are fully transmitted to the second remote computing device; and
    automatically activating, on the second remote computing device, the software application indicated by the electronic token when the at least some of the plurality of images are fully transmitted to the second remote computing device.

2. The method of claim 1 further comprising:
    associating, by the microprocessor of the image server, at least one of the following with the imaging exam: audio or notes.

3. The method of claim 2, wherein at least one of the audio or the notes is transmitted to the first remote computing device based on a user preference of the user.

4. The method of claim 3, wherein the first remote computing device is associated with a patient indicated in the imaging exam.

5. The method of claim 1, wherein the first remote computing device comprises a medical data storage system.

6. The method of claim 5, wherein the medical data storage system comprises at least one of: an electronic medical records system, a storage device local to the user, or a storage device that is shared with multiple users.

7. The method of claim 1, wherein the electronic token is further indicative of a class of software applications.

8. The method of claim 7, wherein the electronic token is generated automatically based on a determination that the software application is compatible with the at least some of the plurality of images.

9. The method of claim 1, wherein the network comprises the Internet.

10. The method of claim 9, wherein the imaging device comprises at least one of: an MRI device, an x-ray device, a mammography device, or a CT scan device.

11. The method of claim 10, wherein the image format indicated by the user preferences includes at least one of: Health Level 7, Portable Document Format, DOC, RTF, XML, HTML, JPEG, GIF, PNG, XLS, PPT, MP3, or WAV.

12. The method of claim 1, wherein the software application is indicated by the executable software code of the electronic token.

13. An image server system comprising:
one or more microprocessors and a memory configured to store software instructions, wherein, when executed by the one or more microprocessors, the software instructions configure the one or more microprocessors to:
store, at the image server system, user preferences of a user, wherein the user preferences include indications of an exam modality, an exam status, an image format, a software application, a transmission schedule, a first storage location, and a second storage location;
receive, from an imaging device over a network, an imaging exam comprising a plurality of images;
receive a report;
associate the report with the imaging exam;
determine that a modality of the imaging exam matches the exam modality indicated by the user preferences;
determine that a status of the imaging exam matches the exam status indicated by the user preferences;
generate an electronic token comprising executable software code, wherein the electronic token includes an indication of the software application indicated by the user preferences;
associate the electronic token with the imaging exam;
in response to determining that a format of at least one image of the plurality of images of the imaging exam is not in the image format indicated by the user preferences, format, by the microprocessor of the image server, the at least one image to match the image format indicated by the user preferences;
transmit the report associated with the imaging exam from the image server to a first remote computing device based on the transmission schedule indicated by the user preferences;
transmit at least some of the plurality of images of the imaging exam and the token from the image server to a second remote computing device when the second remote computing device is connected to the image server and based on the transmission schedule indicated by the user preferences;
automatically generate and transmit, over the network, a notification to the user when the at least some of the plurality of images of the imaging exam are fully transmitted to the second remote computing device; and
automatically activate, on the second remote computing device, the software application indicated by the electronic token when the at least some of the plurality of images are fully transmitted to the second remote computing device.

14. The image server system of claim 13, wherein the network comprises the Internet.

15. The image server system of claim 14, wherein the imaging device comprises at least one of: an MRI device, an x-ray device, a mammography device, or a CT scan device.

16. The image server system of claim 15, wherein the image format indicated by the user preferences includes at least one of: Health Level 7, Portable Document Format, DOC, RTF, XML, HTML, JPEG, GIF, PNG, XLS, PPT, MP3, or WAV.

17. The image server system of claim 13, wherein the first remote computing device is associated with a patient indicated in the imaging exam.

18. The image server system of claim 13, wherein the first remote computing device comprises a medical data storage system.

19. The image server system of claim 18, wherein the medical data storage system comprises at least one of: an electronic medical records system, a storage device local to the user, or a storage device that is shared with multiple users.

20. The image server system of claim 13, wherein the electronic token is further indicative of a class of software applications.

21. The image server system of claim 20, wherein the electronic token is generated automatically based on a determination that the software application is compatible with the at least some of the plurality of images.

22. The method of claim 13, wherein the software application is indicated by the executable software code of the electronic token.

* * * * *

UNITED STATES PATENT AND TRADEMARK OFFICE
CERTIFICATE OF CORRECTION

| | | |
|---|---|---|
| PATENT NO. | : 9,754,074 B1 | Page 1 of 1 |
| APPLICATION NO. | : 14/298806 | |
| DATED | : September 5, 2017 | |
| INVENTOR(S) | : Murray A. Reicher | |

It is certified that error appears in the above-identified patent and that said Letters Patent is hereby corrected as shown below:

On the Title Page

In Column 1 (page 6, item (56)) at Line 22, Under Other Publications, change "2015, 2015" to --2015,--.

In Column 1 (page 6, item (56)) at Line 57, Under Other Publications, change "Browers" to --Browsers--.

In Column 1 (page 7, item (56)) at Line 11, Under Other Publications, change "Incoprorated." to --Incorporated.--.

In Column 1 (page 7, item (56)) at Line 15, Under Other Publications, change "Incoprorated." to --Incorporated.--.

In Column 1 (page 7, item (56)) at Line 22, Under Other Publications, change "Techology" to --Technology--.

In Column 1 (page 7, item (56)) at Line 67, Under Other Publications, change "Healcare," to --Healthcare,--.

In Column 2 (page 7, item (56)) at Line 31, Under Other Publications, change "Vixtek" to --Viztek--.

In the Claims

In Column 12 at Line 53, In Claim 22, change "method" to --system--.

Signed and Sealed this
Eighth Day of May, 2018

Andrei Iancu
*Director of the United States Patent and Trademark Office*